United States Patent
Wang et al.

(10) Patent No.: US 12,357,712 B2
(45) Date of Patent: Jul. 15, 2025

(54) TARGETED RADIOPHARMACEUTICAL FOR TUMOR AND ITS USE IN THE IMAGING-GUIDED COMBINATION THERAPY OF TARGETED RADIOTHERAPY AND IMMUNOTHERAPY

(71) Applicant: Beijing Giluntide Pharmaceutical Co., Ltd., Beijing (CN)

(72) Inventors: Fan Wang, Beijing (CN); Jiyun Shi, Beijing (CN); Hannan Gao, Beijing (CN); Bing Jia, Beijing (CN)

(73) Assignee: Beijing Giluntide Pharmaceutical Co., Ltd., Beijing (CN)

( * ) Notice: Subject to any disclaimer, the term of this patent is extended or adjusted under 35 U.S.C. 154(b) by 767 days.

(21) Appl. No.: 17/310,604

(22) PCT Filed: May 22, 2020

(86) PCT No.: PCT/CN2020/091861
§ 371 (c)(1),
(2) Date: Aug. 12, 2021

(87) PCT Pub. No.: WO2020/238800
PCT Pub. Date: Dec. 3, 2020

(65) Prior Publication Data
US 2023/0117927 A1    Apr. 20, 2023

(30) Foreign Application Priority Data

May 24, 2019 (CN) .......................... 201910441556.7
May 6, 2020 (CN) .......................... 202010373843.1

(51) Int. Cl.
| | | |
|---|---|---|
| *A61K 51/08* | (2006.01) | |
| *A61P 35/00* | (2006.01) | |
| *C07B 59/00* | (2006.01) | |
| *C07K 7/64* | (2006.01) | |

(52) U.S. Cl.
CPC .......... *A61K 51/082* (2013.01); *A61K 51/088* (2013.01); *A61P 35/00* (2018.01); *C07B 59/004* (2013.01); *C07K 7/64* (2013.01)

(58) Field of Classification Search
None
See application file for complete search history.

(56) References Cited

U.S. PATENT DOCUMENTS

| | | | | |
|---|---|---|---|---|
| 2006/0153770 A1* | 7/2006 | DeNardo | .................. | A61P 9/00 514/19.5 |
| 2009/0169575 A1* | 7/2009 | Rohlff | .............. | G01N 33/574 19 435/7.1 |
| 2012/0010229 A1* | 1/2012 | MacDougall | ........... | A61P 35/00 546/15 |

FOREIGN PATENT DOCUMENTS

| | | | |
|---|---|---|---|
| CN | 101474415 A | 7/2009 | |
| CN | 101485891 A | 7/2009 | |
| CN | 104844806 A | 8/2015 | |
| CN | 110227169 A | 9/2019 | |
| CN | 110612126 A | 12/2019 | |
| WO | WO-2008053360 A2 * | 5/2008 | ............. A61P 35/00 |
| WO | WO-2017196806 A1 * | 11/2017 | ......... A61K 51/0497 |
| WO | 2018045376 A2 | 3/2018 | |
| WO | 2018187631 A1 | 10/2018 | |

OTHER PUBLICATIONS

Zheng et al. (Evaluation of 99mTc-3PRGD2 integrin receptor imaging in hepatocellular carcinoma tumour-bearing mice: comparison with 18F-FDG metabolic imaging, May 4, 2017, Annals of Nuclear Medicine, 31:486-494) (Year: 2017).*
Shi et al. (Radiolabeled cyclic RGD peptides as radiotracers for tumor imaging, Apr. 12, 2016, Biophysics Reports, 2(1):1-20) (Year: 2016).*
Liu et al. (Two 90Y-Labeled Multimeric RGD Peptides RGD4 and 3PRGD2 for Integrin Targeted Radionuclide Therapy, Jan. 19, 2011, Molecular Pharmaceuticals, 8:591-599) (Year: 2011).*
Shi (Anti-tumor Effect of Integrin Targeted 177Lu-3PRGD2 and Combined Therapy with Endostar, Jan. 18, 2014, Theranostics, 4(3):256-266) (Year: 2014).*
Lecocq (Theranostics in immuno-oncology using nanobody derivatives, Oct. 15, 2019, Theranostics, 9(25):7772-7791) (Year: 2019).*
Zhang (Structural basis of a novel PD-L1 nanobody for immune checkpoint blockade, Mar. 7, 2017, Cell Discovery, 3:17004). (Year: 2017).*
Chen, Haojun et al.; Novel "Add-On" Molecule Based on Evans Blue Confers Superior Pharmacokinetics and Transforms Drugs to Theranostic Agents, The Journal of Nuclear Medicine vol. 58., No. 4., 22016-11-22, pp. 590-597.
Pang, Hong Bo et al. "A free cysteine prolongs the half-life of a homing peptide and improves its tumor-penetrating activity." Journal of Controlled Release, vol. 175, Dec. 15, 2013, pp. 48-53.
Leung, Kam et al. "68Ga-1, 4, 7, 10-Tetraazacyclododecane-N, N', N", N'''-tetraacetic acid-cyclo(Arg-Gly-Asp-D-Phe-Lys)", Molecular Imaging and Contrast Agent Database, Dec. 10, 2009, entire document.
Zheng, Jieling et al. "Evaluation of 99mTc-3PRGD2 integrin receptor imaging in hepatocellular carcinoma tumour-bearing mice: comparison with 18F-FDG metabolic imaging." Ann. Nucl. Med., vol. 31, No. 6, May 4, 2017, pp. 486-494.

(Continued)

*Primary Examiner* — Michael G. Hartley
*Assistant Examiner* — Kaila A Craig
(74) *Attorney, Agent, or Firm* — McCarter & English, LLP

(57) ABSTRACT

A pharmacological composition contains a complex having a structurally modified RGD polypeptide a radionuclide. This pharmacological composition is useful for diagnosis or treatment of the integrin αvβ3-positive tumors. The pharmacological composition may further contain an immunotherapeutic medicament and an optional nanoantibody molecular imaging probe. Treatment with a PD-L1 blockade after the targeted radioactive therapy can archive the optimal synergic efficacy. Moreover, with administration of PD-1 or PD-L1 nanoantibody molecular imaging probe, expression of PD-1 or PD-L1 in the tumor after targeted radiotherapy can be observed.

14 Claims, 21 Drawing Sheets

(56) References Cited

OTHER PUBLICATIONS

Shi, Jiyun et al. "Anti-tumor Effect of Integrin Targeted 177 Lu-3PRGD2 and Combined Therapy with Endostar" Theranostics, vol. 4, No. 3, Jan. 18, 2014, pp. 256-266.

Chen, Kai. et al. "RGD-Human Serum Albumin Conjugates as Efficient Tumor Targeting Probes." Molecular imaging, vol. 8, No. 2, Apr. 30, 2009, pp. 65-73.

Jin, Xxiaona. et al. "Integrin Imaging with 99m Tc-3PRGD2 SPECT/CT Shows High Specificity in the Diagnosis of Lymph Node Metastasis from Non-Small Cell." Radiology, vol. 281, No. 3, Dec. 31, 2016, pp. 958-966.

Chen, Haojun et al.; "Integrin αvβ3-targeted radionuclide therapy combined with immune checkpoint blockade immunotherapy synergistically enhances anti-tumor efficacy"; Theranostics, vol. 9, No. 25; Oct. 16, 2019; pp. 7948-7960.

Wu, Yue et al.: "Imaging-guided anti-PD-L1 immunotherapy with SPECT/CT of 99m Tc-labeled nanobody"; Journal of Labelled Compounds & Radiopharmaceuticals; vol. 62, May 31, 2019; pp. 443-444.

Zhang, Sufang;"The Second Office Action for CN202010373843.1, title: A Pharmaceutical Composition for Targeted Radiation and Immune Combination Therapy of Tumors"; The state Intellectual Property Office of People's Republic of China; Aug. 2, 2022; pp. 1-9.

Wu, Yifan;"The Second Office Action for CN201910441556.7, title: Nuclear medicine Drug for Structurally Modified RGD Polypeptides"; The state Intellectual Property Office of People's Republic of China; Mar. 4, 2020; pp. 1-4.

* cited by examiner

TARGETED RADIOPHARMACEUTICAL FOR TUMOR AND ITS USE IN THE IMAGING-GUIDED COMBINATION THERAPY OF TARGETED RADIOTHERAPY AND IMMUNOTHERAPY

CROSS REFERENCES TO RELATED APPLICATIONS

The present application is a U.S. national stage entry of International Application No. PCT/CN2020/091861, filed May 22, 2020, which claims the priority of the prior applications of Chinese patent application nos: 201910441556.7, entitled "A nuclear medicine drug of structurally modified RGD polypeptides", submitted to the China State Intellectual Property Office on May 24, 2019, and 202010373843.1, entitled "A pharmacological composition for treatment of a tumor with the combination therapy of targeted radiotherapy and immunotherapy", submitted to the China State Intellectual Property Office on May 6, 2020, the whole content of which are incorporated herein by reference.

FIELD OF THE INVENTION

The present invention is directed to a targeted radiopharmaceutical for tumor which is modified with a RGD polypeptide, and also to a combination therapy with the radiopharmaceutical and immunotherapeutic drugs.

BACKGROUND ART

Persisting growth, invasion and metastasis of malignancies are dependent upon tumor angiogenesis. Integrins are ones of the factors involved in regulation of tumor vascular proliferation and play a key roles in tumor angiogenesis. Among integrins, the action of the integrin $\alpha v \beta 3$ is of the most importance. Integrin $\alpha v \beta 3$ is highly expressed in neovascular endothelial cells in the tumor, and has no or low expression in the normal cells or mature blood vessels. RGD can bind specifically to the integrin $\alpha v \beta 3$ and therefore the RGD-type molecular probes designed by using the specific binding of the RGD to the integrin $\alpha v \beta 3$ has been investigated and utilized extensively. RGD polypeptides have been optimized early or late by researchers at home and abroad through various methods such as adaptation of linear RGDs into cyclic RGDs, modification with a pharmacokinetic linkage agent, e.g. glycosylation of RGDs, linkage of RGD cyclic peptide monomers into a multimer with glutamic acid, insertion of Gly3 or $PEG_4$ chain between two RGD monomers in a dimer by chemical means, etc, to obtain a structurally modified RGD polypeptide.

However, many radiolabeled cyclic RGD monomer peptides have low uptake in tumors, quick clearance in blood, and high uptake in organs such as kidneys and liver, which limit the usage of the cyclic RGD monomer peptides as imaging agents. With the increase in the degree of multimerization, the uptake of radioactive RGD polypeptides in organs such as kidneys, liver and lungs is also increased significantly. Moreover, the higher the degree of multimerization is, the more complicated the synthesis of the polypeptides is, and the higher the cost is. All of these are also the constraints for development of the multimerized RGD probe. The advantages from simple multimerization or modification of RGDs with the pharmacokinetic linking agent of large molecular weight are not significant any more.

Conventional therapies for cancers (such as radiotherapy and chemotherapy) act usually on neoplastic cells themselves and can elicit responses in most of patients. Although these conventional treatment can generate effective responses in the initial stage of cancer, resistance and recurrence will often occur in the later stage, resulting in treatment failure. Differently from the means of action of the above-mentioned conventional therapies, immunotherapies facilitate generation of an anti-tumor response in an organism on its own by activating the immune system of the organism, and are insusceptible to drug resistance. As a big breakthrough in tumor therapy, the immune checkpoint blockade therapy has significant efficacy in immune treatment of a variety of malignant solid tumors. The programmed cell death receptor 1 (PD-1) and its ligand (PD-L1) are the pair of immune checkpoints studied most extensively at present, with it inhibitor medicaments being applied extensively in the clinical medicine. Although the PD1/PD-L1 blockade therapy can elicit significant and persistent response, it has an objective response of about 30% only. How to increase the efficacy of the therapy remains a key issue in immune treatment of tumors at present.

A combination therapy is one of the major means for increasing the efficacy of the PD1/PD-L1 blockade therapy and the efficacy of the immunotherapy can be enhanced by using the anti-tumor immunological effect generated with the conventional therapy. It is believed from the general viewpoint that the radiotherapy can facilitate release of tumor antigens, enhance differentiation, proliferation, function and tumor infiltration of effector T cells, and shows synergy in combination with the immune checkpoint blockade therapy. At present, the combination of radiotherapy with immunotherapy in immune treatment of pulmonary carcinoma exhibits advantages gradually, while the therapeutic strategy therefor remains to be investigated. Compared with the Conventional radiotherapy, the targeted radiotherapy is an internal radiation therapy on the basis of molecular binding in vivo, which is advantageous in treatment of patients with metastatic neoplasms and advanced-stage tumors. However, the targeted radiotherapy is used clinically in the nearer time and the immunological effects elicited by therapy are unsure. Consequently, the study on the combination therapy of targeted radiotherapy and immunotherapy is insufficient. A nanoantibody probe prepared by using PD-L1 as a biomarker can be used to monitor the tumor microenvironment non-invasively, real-time and dynamically, which is beneficial to direct development of the individualized strategy of the combination therapy of targeted radiotherapy and immunotherapy and increase the effectiveness in immune treatment of tumor.

SUMMARY OF THE INVENTION

To address the above-mentioned issues found in the state of the art, the present invention provides a structurally modified RGD polypeptide of the following formula:

A-(L)n-RGD polypeptide,
wherein
A has the structure below:

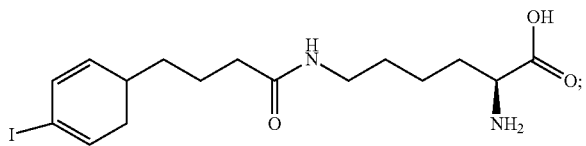 [SMILES: N[C@@H](CCCCNC(=O)CCCC1C=CC(I)=CC1)C(=O)O]

L represents a linking arm molecule with the following structure:

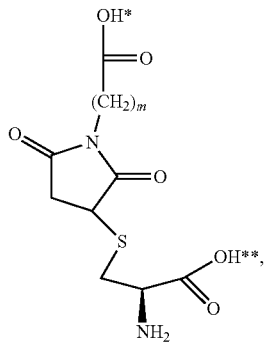

wherein m is an integer from 1 to 8, e.g. from 2 to 6, preferably 5;

the said L is bonded to A by reacting its carboxyl group with an amino group in A, for example, via a *-marked carboxyl group in L bonded with A;

n is 0 or 1;

when n is 0, said RGD polypeptide is bonded by reacting its amino group with a carboxyl group in A;

when n is 1, said RGD polypeptide is bonded by reacting its amino group with another carboxyl group in L, for example, bonded by reacting the **-marked carboxyl group in L with the RGD polypeptide when the *-marked carboxyl group in L is linked to A;

TRGD polypeptide is selected from the group consisting of c(RGDfV), c(RGDfK), c(RGDfE), c(RGDyk), E[c(RGDyk)]$_2$, E[c(RGDfK)]$_2$, and 3PRGD$_2$.

The present invention further provides a radionuclide-labelled complex which comprises the structurally modified RGD polypeptide as above and has a structure as defined below:

Nu-BFC-A-(L)n-RGD polypeptide,
wherein
Nu is a radionuclide, e.g., a diagnostic imaging nuclide: $^{111}$In, $^{64}$Cu, $^{99m}$Tc, $^{68}$Ga, or a therapeutic nuclide: $^{90}$Y, $^{177}$Lu, $^{89}$Sr, $^{153}$Sm, $^{188}$Re;

BFC is a bifunctional chelator, e.g., HYNIC (hydrazine nicotinamide), MAG$_2$ (mercaptoacetyl diglycine), MAG$_3$ (mercaptoacetyl triglycine), DTPA (diethylene triamine pentaacetic acid), DOTA (1,4,7,10-tetraazacyclododecane-1,4,7,10-tetraacetic acid), NOTA (1,4,7-triazacyclononane-1,4,7-tricarboxylic acid), TETA (1,4,8,11-tetraazacyclotetradecane-1,4,8,11-tetraacetic acid);

when n is 0, the said bifunctional chelator is bonded by reacting the carboxyl group in its structure with -NH$_2$ in A;

when n is 1, the said bifunctional chelator is bonded by reacting the carboxyl group in its structure with -NH$_2$ in L.

According to the present invention, in the structurally modified polypeptide RGD and the complex as set forth above, the RGD polypeptide is selected from the group consisting of: c(RGDfK) and 3PRGD$_2$;

Nu is selected from the group consisting of: $^{90}$Y, $^{177}$Lu, $^{111}$In, $^{64}$Cu, $^{99m}$Tc; the BFC is selected from the group consisting of DTPA and DOTA upon Nu being $^{90}$Y, $^{177}$Lu; and the BFC is selected from the group consisting of HYNIC, MAG$_2$, MAG$_3$, DTPA, DOTA, NOTA, and TETA upon Nu being $^{111}$In, $^{64}$Cu, $^{68}$Ga, $^{99m}$Tc.

According to the present invention, the BFC is selected from the group consisting of DTPA and DOTA upon Nu being $^{90}$Y or $^{177}$Lu; the BFC is selected from the group consisting of DTPA and DOTA upon Nu being $^{111}$In; the BFC is selected from the group consisting of TETA and DOTA upon Nu being $^{64}$Cu; the BFC is selected from the group consisting of NOTA and DOTA upon Nu being $^{68}$Ga; and the BFC is selected from the group consisting of HTNIC, DTPA, MAG$_2$, MAG$_3$ upon Nu being $^{99m}$Tc.

As an example, the complex formed with the structurally modified polypeptide of the invention is set forth as follows:

$^{68}$Ga-DOTA-A-c(RGDfk);

$^{99m}$Tc-HYNIC-A-3PRGD$_2$;

$^{177}$Lu-DOTA-A-L-3PRGD$_2$.

It should be understood that all of the isoforms of the structurally modified polypeptide mentioned above in the present invention, including the enantiomers, diastereoisomers and racemates thereof, fall within the scope of the invention. The present invention comprises both the optically pure forms of the stereoisomers or the mixtures thereof and the racemic mixtures thereof. For example, the amino group in the structure A or L in the above-mentioned polypeptide exists in L- or D-configuration.

It is well-known to those skilled in the art that the complex defined above also needs a coligand when the bifunctional chelator as a ligand is unable to occupy all of the coordination sites of the radionuclide. The radionuclide and the bifunctional chelator which need a coligand in the present invention are well known to those skilled in the art. For example, when HYNIC serves as a bifunctional chelator for $^{99m}$Tc, the coligands therefor may be the same or different and are all known in the prior art, among which the common coligands include the water-soluble phosphines (e.g. sodium 3,3',3''-phosphinetriyltribenzenesulfonate (TPPTS)), N-tris(hydroxymethyl)methylglycine (Tricine), N,N-bis(hydroxyethyl)glycine, glucoheptonate salt, ethylenediamine-N,N'-diacetate (EDDA), 3-bis(hydroxyethyl) glycine, glucoheptonate salt, ethylenediamine-N,N'-diacetate (EDDA), 3-benzoylpyridine (BP), pyridine-2-azo-p-dimethylaniline(PADA), etc. For example, when HYNIC serves as a bifunctional chelator for $^{99m}$Tc, TPPTS and Tricine are the coligand. Moreover when DOTA serves as a bifunctional chelator for $^{177}$Lu or $^{68}$Ga, for example, there is no need for a coligand to coordinate.

As an example, present invention provides a complex of a following structure:

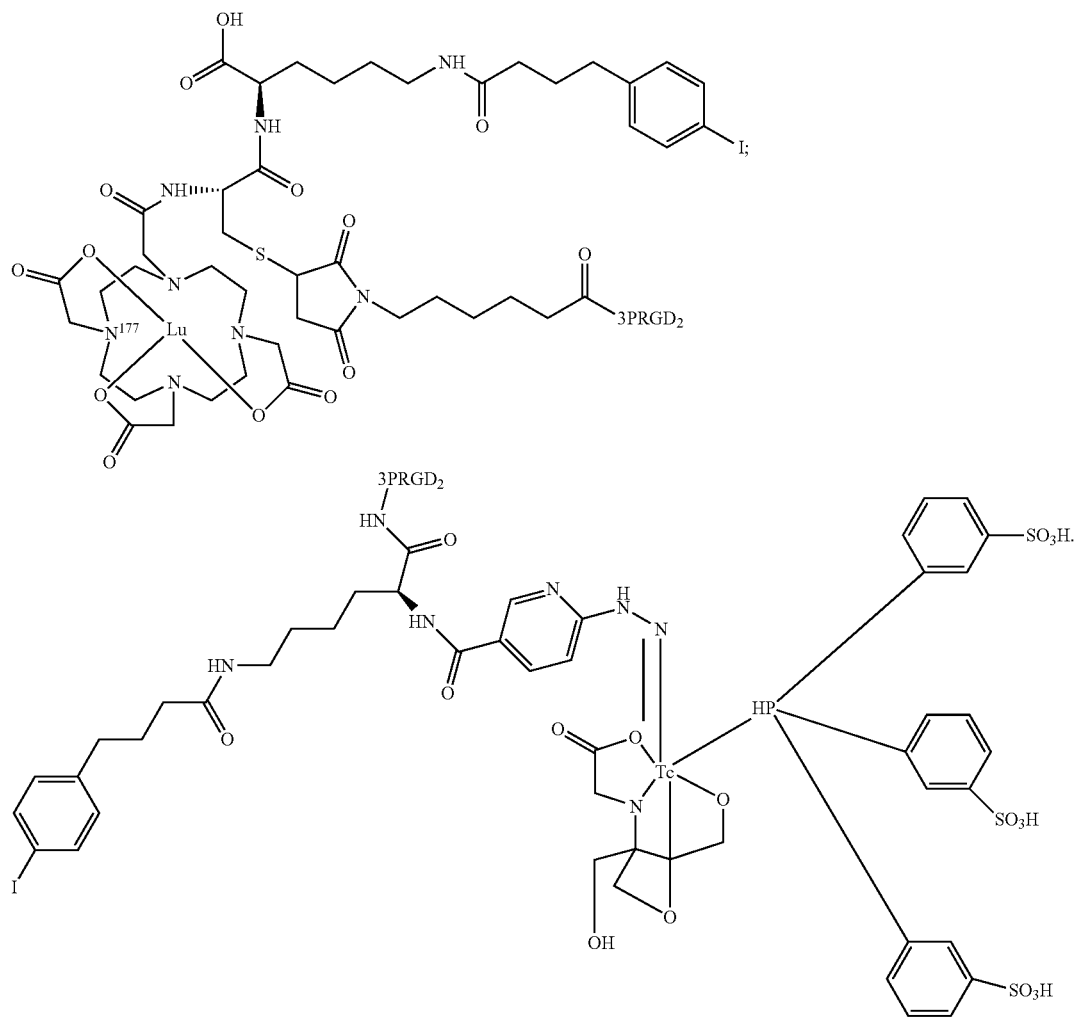

The present invention further provides a molecular probe having the structure of the above-mentioned complex.

The present invention further provides a pharmacological composition comprising an effective amount of the labelled Nu-BFC-A-(L)n-RGD polypeptide complex mentioned above.

According to the present invention, the pharmaceutical compositions of the invention is a diagnostic agent when Nu is a diagnostic nuclide, e.g. the said agent is a imaging agent useful for imaging diagnosis of integrin αvβ3-positive tumors. The agent is administered directly to an individual to make a diagnosis by detecting a ray emitted from the agent which has been administered to the subject and imaging on the basis of the information acquired with this ray. Preferably, the diagnostic agent of the invention is an injectable formulation comprising the labelled complex mentioned above and an injectable carrier. It is preferable that the imaging agent refers to positron emission tomography scan (PET) and single photon emission computed tomography (SPECT).

According to the present invention, the pharmaceutical compositions of the invention is a therapeutic agent when Nu is a therapeutic nuclide, e.g. the said agent is useful for targeted radioactive treatment of integrin αvβ3-positive tumors. The agent is administered directly to an individual and enriched within tumor issues due to its having a specific affinity for the integrin αvβ3. The radionuclide destroys the pathologically altered tissue by emitting pure beta-rays or beta-rays accompanied with gamma-rays to generate biological effects of ionizing radiation. Preferably, the therapeutic agent of the invention is an injectable formulation comprising the labelled complex mentioned above and an injectable carrier.

According to the present invention, the pharmaceutical compositions of the invention can also comprise an immunotherapeutic medicament when Nu is a therapeutic nuclide. In this case, a targeted radiotherapy will be performed with the labelled complex of the invention mentioned above in combination with the immunotherapeutic medicament, to archive the synergic therapeutic effect.

According to the targeted radiotherapy described above in the present invention and the pharmacological composition in combination with the immunotherapy, the preferable labelled complex described above is $^{177}$Lu-DOTA-A-L-3PRGD$_2$. The preferable immunotherapeutic medicament is a PD-1 or PD-L1 immune checkpoint inhibitor. Preference is given to PD-1 or PD-L1 monoclonal antibody drug. The PD-1 or PD-L1 monoclonal antibody drug of the invention are not particularly limited and are the active and effective ones known in the art which target the PD-1/PD-L1 immunological pathways in the human being or animals, e.g. various PD-1 monoclonal antibody medicaments which have been marketed, e.g. Opdivo (MDX-1106), Keytruda (MK-3475), CT-011; or PD-L1 monoclonal antibody, e.g. MDX-1105, MPDL 3280 A, or MEDI 4736; or other PD-1 or PD-L1 monoclonal antibodies known under the stages in clinical trials. The exemplary PD-L1 monoclonal antibody used in the inventive embodiments is (10F.9G$_2$).

It is known to those skilled in the art that, PD-L1 is a ligand for PD-1. After binding to the PD-1 on the surface of a lymphocyte in the healthy and normal status of an organism, the PD-L1 on the surface of a cell can suppress the function of lymphocytes and induce apoptosis of the activated lymphocytes, therefore playing a vital role in autoimmune tolerance and prevention of autoimmune disease. Nonetheless, since PD-L1 would be overexpressed in tumor tissues and PD-1 is highly expressed in the tumor-infiltrating lymphocytes, PD-1 binds to PD-L1, thus suppressing the functions and the tumor killing of the lymphocytes, inducing apoptosis of the lymphocytes, weakening the anti-tumor immune response of the organism itself, and eventually resulting in the occurrence of the immune escape for tumors. Antibodies against PD-1 or PD-L1 can block PD-1/PD-L1 pathways in vivo, therefore facilitating Lymphocyte proliferation, activating the immune system and promoting the generation of anti-tumor response in the organism itself, which further leads to tumor regression. It can be known on the basis of the above-mentioned mechanism that any of the PD-1 or PD-L1 immune checkpoint inhibitors can block the PD-1/PD-L1 pathways and accomplish an anti-tumor response on itself, therefore treating tumors or cancers. Therefore, the PD-1 or PD-L1 monoclonal antibody drug of the invention are not particularly limited, and any of such known medicaments can be useful for the present invention.

The pharmacological composition of the invention for use in the combination of the targeted radiotherapy and the immunotherapy also comprise a nanoantibody molecular imaging probe, e.g. a PD-1 or PD-L1 nanoantibody molecular imaging probe. Preference is given to a PD-L1 nanoantibody technetium label. The exemplary nanoantibody molecular imaging probe used in the inventive embodiments is $^{99m}$Tc-MY1523.

According to the pharmacological composition of the invention for use in the combination of the targeted radiotherapy and the immunotherapy, the said nanoantibody molecular imaging probe is a PD-L1 nanoantibody comprising LPETG tag (MY1523), which can be prepared by linking to $^{99m}$Tc-HYNIC-GGGK with Sortase A enzyme.

According to the pharmacological composition of the invention for use in the combination of the targeted radiotherapy and the immunotherapy, the said labelled complex and the immunotherapeutic medicament can be administered simultaneously or separately. For example, the said immunotherapeutic medicament can be administered after the labelled complex, and preferably, the said immunotherapeutic medicament is administered 3 to 6 days after administration of the labelled complex.

According to the pharmacological composition of the invention for use in the combination of the targeted radiotherapy and the immunotherapy, the said nanoantibody molecular imaging probe is administered after administration of the labelled complex and before administration of the immunotherapeutic medicament.

Preferably, the labelled complex, the immunotherapeutic medicament or the nanoantibody molecular imaging probe of the invention is an injectable formulation comprising the labelled complex, the immunotherapeutic medicament or the nanoantibody molecular imaging probe mentioned above and an injectable carrier.

Preferably, the pharmacological composition of the invention is an intravenous injection, e.g. a colorless, clear, liquid injection. Excipients suitable for intravenous injections are generally known in the art and the said pharmacological composition may be formulated in aqueous solution, if necessary, using physiologically compatible buffers, for example including phosphate, histidine, citrate, etc., to adjust the pH of the formulation. A tonicity agent also can be used, such as sodium chloride, sucrose, glucose, etc. Furthermore, a co-solvent can be used, e.g. polyethylene glycol, as the same with a low toxic surfactant, e.g. polysorbate or poloxamer, etc.

Preferably, the pharmacological composition of the invention further comprise an anti-absorbent, e.g. normal saline, aqueous solution of 1% cyclodextrin, and/or PBS solution with Tween-20 (e.g. with the mass fraction of 0.01% to 0.1% Tween-20). Upon administration of the pharmacological composition of the invention comprising an anti-sorbent, using a solution of a surfactant such as Tween-20 (e.g. 0.05% in parts by mass) can be effective to avoid non-specific adsorption of the label in the fusion and prevent substantially the radioactive label from absorbing to the wall of the infusion line, thus achieving the precision of dosage and allowing the dosage to be administered precisely while abstaining from wasting the medicament during administration. The recovery of the label can be above 97% when the pharmacological composition comprising the above-mentioned anti-sorbent is transferred consecutively 4 times in a serial of new Eppendorf tubes.

According to the present invention, a kit is also provided, which is loaded respectively with the labelled Nu-BFC-A-(L)n-RGD polypeptide complex as set forth above in the present invention, an immunotherapeutic medicament, and an optional nanoantibody molecular imaging probe.

According to the present invention, the use of the above-mentioned A-(L)n-RGD polypeptide or Nu-BFC-A-(L)n-RGD polypeptide molecular probe or the above-mentioned pharmacological composition in preparation of a medicament is also provided. According to the present invention, the medicament is used to diagnosis or treat a integrin αvβ3-positive tumor, the tumor referring to a solid tumor, e.g. a malignant neoplasm in the sites such as blood, liver, glands (e.g. mammary gland, prostate gland, pancreas), intestine (e.g. colon, rectum), kidney, stomach, spleen, lung, muscular, bone, etc.

The present invention further provides a method for diagnosing or treating a hematologic and solid malignancies with highly expressed integrin αvβ3, comprising administration of an effective amount of the above-mentioned Nu-BFC-A-(L)n-RGD polypeptide to an individual in need thereof. According to the present invention, the individual may be a mammalian, such as a human beings.

The present invention further provides a method for treating a hematologic and solid malignancies with highly expressed integrin αvβ3, comprising administration of an effective amount of the labelled Nu-BFC-A-(L)n-RGD polypeptide complex and an immunotherapeutic medicament to an individual in need thereof. According to the present invention, the individual may be a mammalian, such as a human beings.

According to the method of the invention, the immunotherapeutic medicament is administered after administration of the labelled complex, e.g. 3 to 6 days after the administration thereof.

According to the method of the invention, the labelled complex and the immunotherapeutic medicament is administered in the form of injection.

According to the method of the invention, the method is performed under the direction of the nanoantibody molecular imaging probe. For example, the technetium-labelled nanoantibody is used to monitor PD-L1 expression in the tumor in vivo after administration of the labelled complex.

According to the method of the invention, basing on monitoring the PD-L1 expression, the immunotherapeutic medicament is administered when PD-L1 expression is increased or peaks.

Terms and Definitions

Unless defined otherwise, all technical and scientific terms used herein have the same meaning as commonly understood by those skilled in the art to which the subject matter of the claims pertain. Unless specified otherwise, the full contents of all patents, patent applications, publications cited herein are hereby incorporated herein by reference in their entirety.

When a numerical range documented in the present application the specification and claims is understood as an "integer", it should be understood to document two end points of the range and each of the integers within the range. For example, an "integer from 0 to 10" should be understood to document each of the integers of 0, 1, 2, 3, 4, 5, 6, 7, 8, 9 and 10. When the numerical range is understood as a "number", it should be understood to document two end points of the range and each of the integers within the range. For example, an "integer from 1 to 10" should be understood to not only document each of the integers of 1, 2, 3, 4, 5, 6, 7, 8, 9 and 10, but also document at least the sum of the each of the integers thereof and 0.1, 0.2, 0.3, 0.4, 0.5, 0.6, 0.7, 0.8, 0.9, respectively.

RGD Polypeptides: All are the known substance in the art. RGDs are small-molecule polypeptides comprising an amino acid sequence of arginine-glycine-asparitic acid (Arg-Gly-Asp). With addition of D-phenylalanine and D-valine, a cyclic pentapeptide structure of c(RGDfV) is synthesized, wherein c indicates the polypeptide being circle, R represents arginine, G represents glycine, D represents asparitic acid, f represents D-phenylglycine, and V represents valine.

Substitution of five amino acids in the cyclic pentapeptide structure of c(RGDfV) with other amino acids results in c(RGDfK), c(RGDfE), c(RGDyk), wherein K is lysine, E is glutamic acid, and y is D-tyrosine. For example, c(RGDfK) have the following structure:

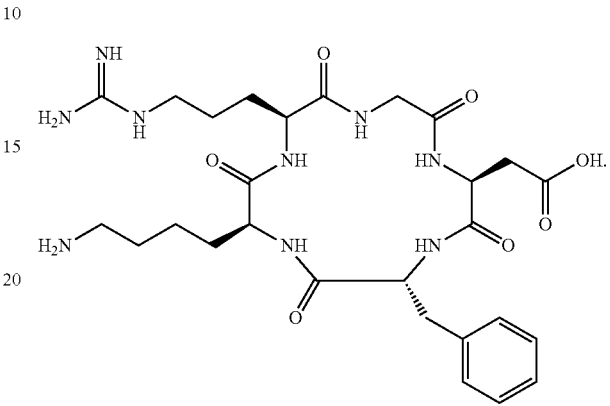

These cyclic peptide structures can form dimers, e.g. E[c(RGDyk)]$_2$ and E[c(RGDfK)]$_2$, resulting from joining two cyclic RGD peptides with glutamic acid. 3PRGD$_2$ refers to a dimer consisting of two of cyclic RGD pendtapeptides modified with three of polyethylene glycols, namely PEG$_4$-[PEG$_4$-c(RGDXk)]$_2$, wherein X is D-phenylglycine, D-tyrosine, etc. An exemplary schematic for its structure as follows:

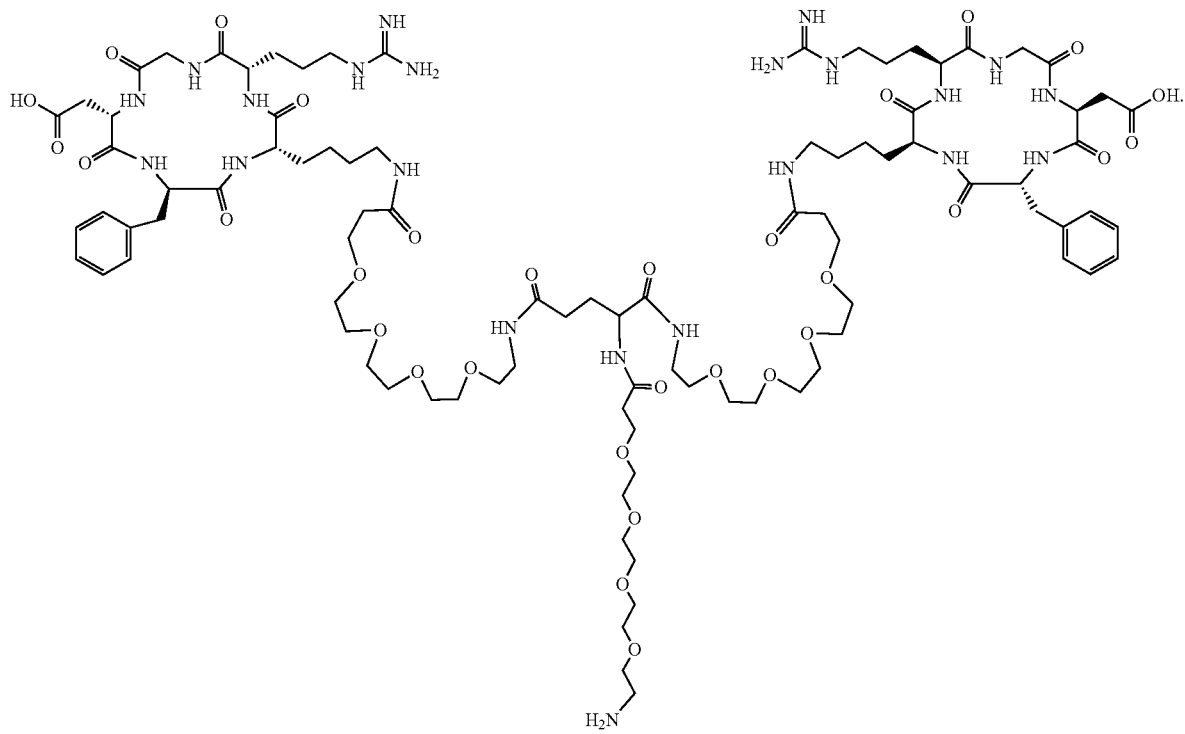 [SMILES: N=C(N)NCCC[C@@H]1NC(=O)[C@H](CCCCNC(=O)CCOCCOCCOCCOCCNC(=O)CCC(NC(=O)CCOCCOCCOCCOCCN)C(=O)NCCOCCOCCOCCOCCC(=O)NCCCC[C@@H]2NC(=O)[C@@H](Cc3ccccc3)NC(=O)[C@H](CC(=O)O)NC(=O)CNC(=O)[C@H](CCCNC(=N)N)NC2=O)NC(=O)[C@@H](Cc2ccccc2)NC(=O)[C@H](CC(=O)O)NC(=O)CNC1=O]

Bifunctional Chelator: A bifunctional chelator (BFC) refers to a functional organic material which both can link covalently to a biological molecule and chelate to a metal nuclide and whose structure can insure a firm binding to the metal nuclide and the introduced metal nuclide being far away from the biological molecule to avoid surely of impairing the bioactivity of the molecule, thus leading to a stable nuclide-chelator-biological molecule marker. The bifunctional chelators used in the present invention are those known in the prior art such as HYNIC (hydrazino nicotinamide), $MAG_2$ (mercaptoacetyl diglycine), $MAG_3$ (mercaptoacetyl triglycine), DTPA (diethylene triamine pentaacetic acid), DOTA (1,4,7,10-tetraazacyclododecane-1,4,7,10-tetracetic acid), NOTA (1,4,7-triazacyclononane-1,4, 7-tricarboxylic acid), TETA (1,4,8,11-tetraazacyclotetradecane-1,4,8,11-tetraacetic acid), etc.

The term "treatment" and other similar synonyms thereof herein used include ameliorating, alleviating or improving symptoms of diseases or disorders, preventing other symptoms thereof, ameliorating or preventing potential metabolic cause which results in symptoms, suppressing diseases or disorders, e.g. hindering the development of diseases or disorders, ameliorating diseases or disorders, improving diseases or disorders, ameliorating symptoms caused by diseases or disorders, or interrupting symptoms of diseases or disorders. In addition, the term encompasses the purpose of prophylaxis. The term further encompasses obtaining therapeutic and/or prophylactic effects. The said therapeutic effect refers to curing or ameliorating the potential disease treated. In addition, curing or ameliorating one or more physiologic symptoms associated with the potential disease is also the therapeutic effect, e.g. the improved condition of a patient is observed, while the patient may suffer from the potential disease nevertheless. For the prophylactic effect, the said composition can be administered to a patient at the risk of a particular disease or to a patient presenting one or more physiologic symptoms of the disease even if the disease has not been diagnosed.

Advantageous Effects

In the present invention, the structurally modified RGD polypeptides have been designed and prepared and a series of novel RGD polypeptide molecular probes have been prepared from the structurally modified RGD polypeptides. It has been found in the present invention that by modifying and adapting the structure of the said RGD polypeptide, the molecular probe of the invention formed with the structurally modified RGD polypeptide together with the chelator and the radionuclide has a higher in vivo stability and a higher albumin-binding rate, therefore a significantly extended half-life; and that the molecular probe of the invention has a higher tumor uptake rate, higher contrast, and higher safety, which reduce the dosage used and side effects, therefore improving the imaging performance of the serial RGD probes as a molecular probe for diagnostic imaging in SPECT and/or PET and the efficacy thereof as a molecular probe for therapy in the targeted radioactive therapy.

An example of the novel molecular probe of the invention $^{177}$Lu-DOTA-A-L-3PRGD$_2$, has a high uptake in blood, therefore increasing the uptake in tumors. The accumulated uptakes of the probe in blood and in tumors are about 8 times and about 4 times that for the original probe, respectively. Tumor uptake of the novel probe peaks 4 hours after injection with the percent injected doses per gram of 26.52±0.58% ID/g. and sharp imaging was still enabled 48 hours after injection. This property increases significantly the imaging performance of the serial RGD probes as a molecular probe for diagnostic imaging and the efficacy thereof as a therapeutic molecular probe for the targeted radioactive therapy.

The targeted radiation therapy medicament set forth in the present invention not only can be enriched specifically in the tumor tissues and act directly on tumor cells via internal radiation, but also can activate the body to generate T cell-mediated anti-tumor immune response. In an embodiment of the invention, the targeted radiotherapy induce the remodeling of the tumor immune microenvironment, increases significantly the infiltration of CD4$^+$ and CD8$^+$ T lymphocytes (rather than T-reg cells) into tumor tissues, and up-regulate the expression level of PD-L1 on the surface of myeloid immune cells (rather than tumor cells).

The present invention by using PD-1/PD-L1 immune checkpoint inhibitors in combination can be effective in increasing the activation of naive T cells and effector phase of the effector T cells, which play an important role in the early and later periods of the tumor immunity cycle. Furthermore, the targeted radiopharmaceutical modified with the RGD polypeptide of the invention facilitate the antigen releasing of tumors and the antigen presentation of immune cells, playing an important role in the early period of the tumor immunity cycle. Therefore, the invention makes good use of the same and different periods in the tumor immunity cycle to accomplish the activation of the anti-tumor immunity in the presence of the synergy of targeted radiation therapy and immunotherapy. In addition, the present invention further use PD-L1 nanoantibody molecular imaging probe to monitor the changes in PD-L1 expression under tumor microenvironment during the treatment, in order to direct dosing schedule for the combination therapy.

When the labelled nuclide is a therapeutic nuclide, the labelled complex of the invention is an effective targeted radiotherapy medicament which can treat effectively the tumor in a MC-38 syngeneic tumor model of normal immunity. In an embodiment of the invention, the administration of 18 MBq of the labelled complex can ablate totally the tumor by the T cell-mediated specific immune response. The remodeling of tumor immune microenvironment induced by the targeted radiotherapy of the invention is embodied primarily by: increasing significantly the infiltration of CD4+ and CD8+ T lymphocytes (rather than T-reg cells) and up-regulating the PD-L1 expression on the surface of myeloid immune cells (rather than tumor cells) in the tumor, due to treatment of tumors with internal radiation. Immunosuppression is most severe on Day 6 of administration of the targeted radiopharmaceutical, in which PD-L1 expression in tumors is highest. Therefore, PD-L1 blockade therapy 3-6 days after the targeted radiotherapy can archive the optimal synergic efficacy.

Additionally, it is found experimentally in the present invention that the synergic efficacy can be obtained only by administering the PD-L1 monoclonal antibody in the time window in PD-L1 is increased dynamically. Consequently, following-up the dynamic changes in PD-L1 expression after the targeted radiotherapy is of important guiding significance. With administration of PD-1 or PD-L1 nanoantibody molecular imaging probe of the invention, expression of PD-L1 in the tumor after targeted radiotherapy can be observed, which has guiding significance in establishing therapeutic strategy for the combination therapy of targeted radiotherapy and immunotherapy and helps to increase the effect of the combination therapy.

BRIEF DESCRIPTION OF THE DRAWINGS

FIG. 1A is the chromatogram before purification and FIG. 1B is the chromatogram after purification.

FIG. 14A shows a targeted radiotherapy with different dosages administered (n=7); FIG. 14B shows the changes in the body weight of the mouse during the treatment (n=7); FIG. 14C shows a treatment experiment in which immune exhaustion is performed with CD8 antibodies in the targeted radiotherapy (n=7).

FIG. 15A shows the percentage of T lymphocytes in the tumor digestive cells in the tumor tissue after treatment with 0 to 18 MBq of $^{177}$Lu-DOTA-A-L-3PRGD$_2$ (n=4); FIG. 15B shows PD-L1 expression on tumor cells and myeloid cells (n=4). Cell grouping: CD8$^+$ T cells (CD45$^+$CD3e$^+$CD8$^+$), CD4$^+$ T cells (CD45$^+$CD3e$^+$CD4$^+$), T-reg cells (CD45$^+$CD3e$^+$CD4$^+$Foxp3$^+$), tumor cells (CD45$^-$), myeloid cell (CD45$^+$CD11b$^+$).

FIG. 16A is dynamic imaging 0, 3 and 6 days after treatment with 9 MBq of $^{177}$Lu-DOTA-A-L-3PRGD$_2$ (n=3, *P<0.05); FIG. 16B is the imaging at Day 6 after treatment with 0, 9 and 18 MBq of $^{177}$Lu-DOTA-A-L-3PRGD$_2$ and the background imaging after treatment at a dose of 18 MBq.

FIG. 17A is the Biodistribution of $^{99m}$Tc-nanoantibody 2 hrs after being injected into the mouse, at Day 6 after treatment with 0 to 18 MBq of $^{177}$Lu-DOTA-A-L-3PRGD$_2$. FIG. 17B is the linear analysis on PD-L1 expression on myeloid cells within the tumor and the uptake of $^{99m}$Tc-nanoantibody into the tumor.

FIG. 18A shows the dynamic changes in PD-L1 on tumor cells and myeloid cells in the tumors microenvironment 3 to 12 days after treatment with 9 MBq of $^{177}$Lu-DOTA-A-L-3PRGD$_2$ (n 25=4), FIG. 18B shows the single anti-PD-L1 combination therapy administered 3 to 12 days after the targeted radiotherapy (n=7, **P<0.01).

FIG. 19A is the single anti-PD-L 1 blockade therapy at the different time points (n=7);

FIG. 19B is the anti-PD-L1 blockade combination therapy after neutralization , before the targeted radiotherapy and (n=7); FIG. 19C is the survival rate of mice for the combination therapy (n=7).

DETAILED DESCRIPTION

Figure 1A:
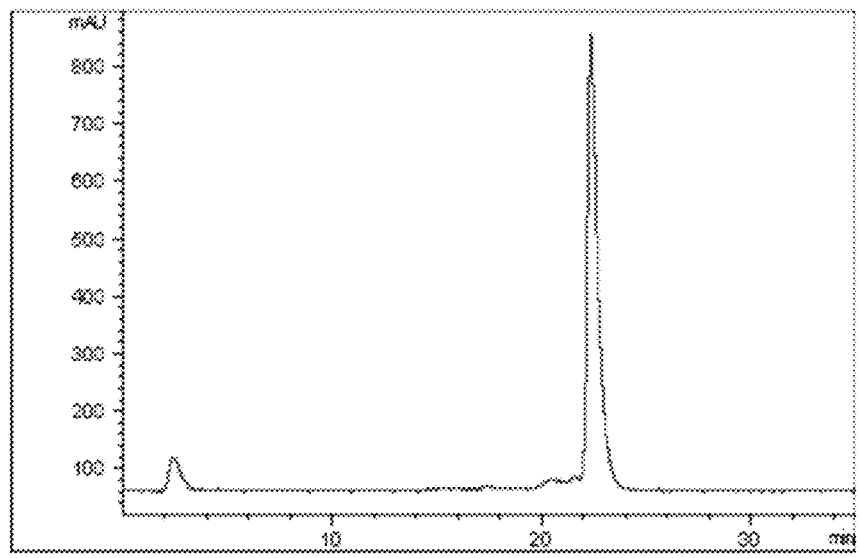
FIGS. 1A-1B: The chromatogram of radio-HPLC for $^{68}$Ga-DOTA-A-c(RGDfk), the final product of Example 1.

The above and other characteristics and advantages of the invention will be explained and illustrated below in more details by describing the Examples of the invention. It should be understood that the Examples below are intended to illustrate exemplarily the technical solutions the present invention, but not to limit in any way the scope of protection of the invention defined in the claims and the equivalents thereof.

Unless otherwise specified, materials and reagents herein are all the commercially available products, or can be prepared according to the state of the art by the person of skill.

It should be understood by those skilled in the art that the starting materials, reagents, intermediates, the target compounds or reaction formulas in the Examples below are all exemplary technology solutions for the compounds of general formula hereinabove or the reaction therefor, where one or more of the particular compounds or the particular reaction formulas all can be combined with generic technology solutions of the invention, and the technology solution arising after the combination should be construed as the technology solution documented in the specification.

Statistical analysis

The experimental results are expressed in the form of the mean±standard deviation (mean±SD). The results are analyzed statistically for intergroup difference with Analysis of Variance and t test. P<0.05 is believed to be statistically different (*).

EXAMPLE 1
Preparation of $^{68}$Ga-DOTA-A-c(RGDfk)
The schematic pathway for synthesizing DOTA-A-c(RGDfk) is as follows:
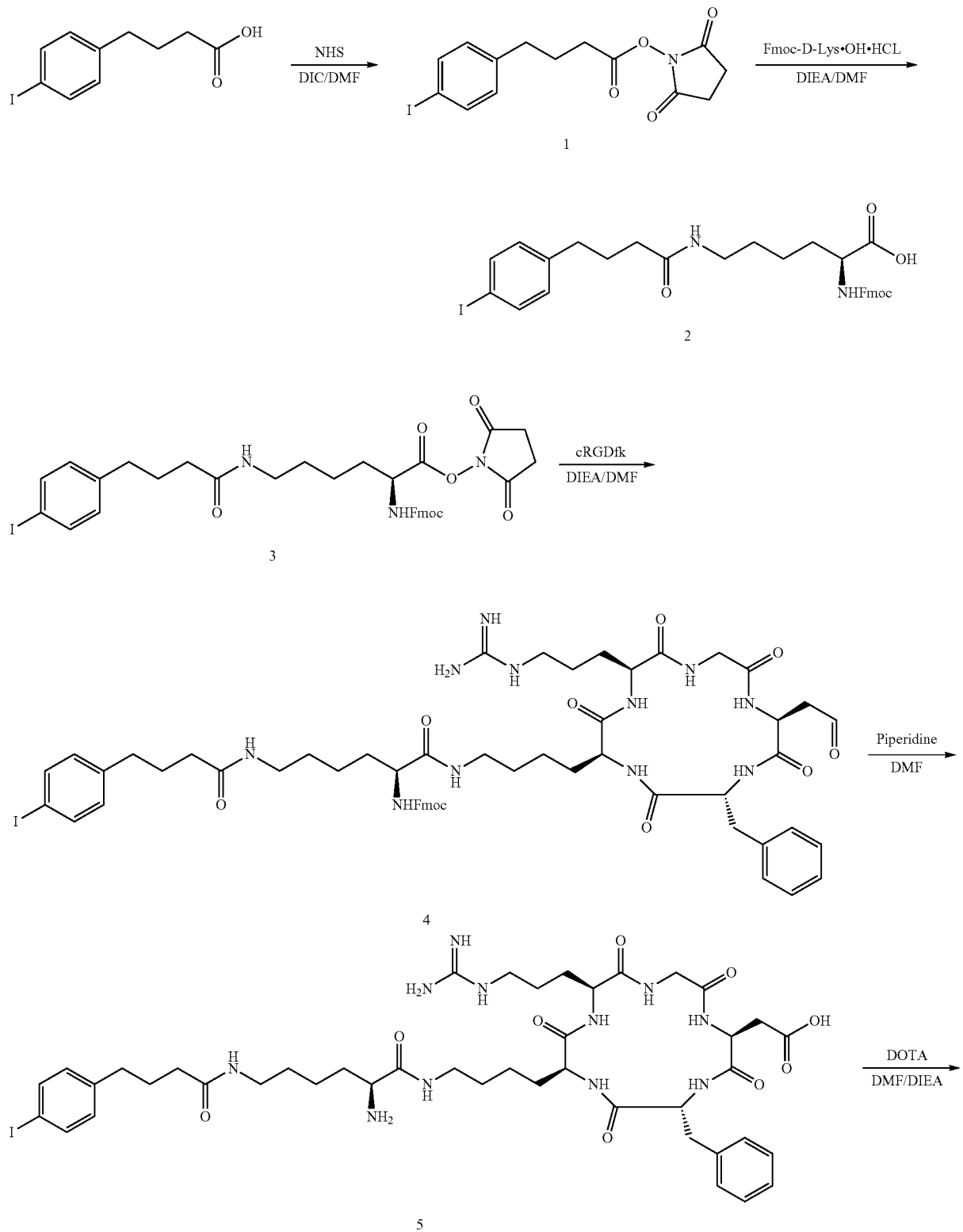

-continued

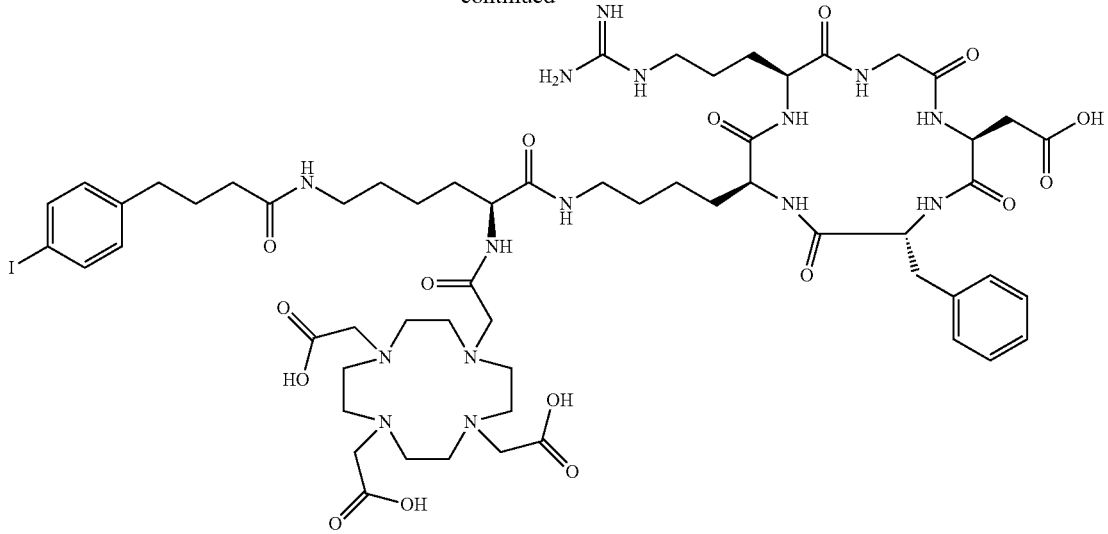

6

(1) Synthesis of Compound 1

4-(4-iodophenyl)butanoic acid (9.8 mg, 33.8 mmol) is weighed, added into a single-port flask, and dissolved in 400 μL of DMF. NHS (3.9 mg, 33.9 mmol) is added. Furthermore, 5.3 μL of DIC is added. The reaction is stirred thermostatically at 30° C. for 2 h and monitored by TLC (ethyl acetate:petroleum ether:acetic acid=100:200:2) until disappearance of the starting materials. Upon completion of the reaction, the reaction solution is dissolved in ethyl acetate and washed with water three times. The ethyl acetate phase is dried over anhydrous sodium sulphate, concentrated and then isolated by column chromatography (ethyl acetate:petroleum ether:acetic acid=100:200:2). Fractions are collected and tested. The collected product is subjected to rotary evaporation to dryness, resulting in 10.2 mg of a white solid with a yield of 78%. The resulting product is confirmed by MALDI-TOF mass spectrometry analysis to be the expected product.

MS (ESI): m/z=387.2137 (the chemical formula: $C_{14}H_{14}INO_4$ and the calculated molecular weight: 387.00). A small amount of the solid was obtained, weighed, re-dissolved and identified by HPLC to be of >98% purity.

(2) Synthesis of Compound 2

Compound 1 (20 mg, 51.7 mmol) is weighed, added into a round-bottomed flask with 500 μL of DMF and dissolved. Then, Fmoc-D-Lys.HCL (22.8 mg, 56.3 mmol) is weighed and added into the flask. 12 μL of DIEA is added to adjust the pH to be 8.5. The reaction is stirred thermostatically at 30° C. for 0.5 h and monitored by TLC (ethyl acetate:petroleum ether:acetic acid=100:200:1) until disappearance of the starting materials. After completion of the reaction, the reaction solution is dissolved in 20 mL of ethyl acetate, washed respectively with 20 mL of saturated sodium chloride solution and 20 mL of water three times. The ethyl acetate layer is dried over anhydrous magnesium sulphate and subjected to rotary evaporation under reduced pressure to dryness, resulting in a yellow viscous liquid of 26.5 mg. The yield is 85%. The resulting product is confirmed by MALDI-TOF mass spectrometry analysis to be the expected product.

MALDI-TOF-MS: m/z=1718.33 (M+H)$^+$, 1741.02 (M+Na)$^+$ (the chemical formula: $C_{80}H_{119}N_{25}O_{16}S$ and the calculated molecular weight: 1719.02 Da.). A small amount of the product is obtained, weighed, re-dissolved and assayed by HPLC to be of 96.7% purity.

(3) Synthesis of Compound 3

Compound 2 (10 mg, 15.6 mmol) is weighed, added into a single-port flask, and dissolved in 500 μL of DMF, followed by addition of NHS (1.83 mg, 15.9 mmol). Furthermore, 4 μL of DIC is added into the single-port flask. The reaction is stirred at 35° C. for 35 minutes. When being heated for min, the suspension is found to become clear. The reaction is monitored by TLC (ethyl acetate:petroleum ether:acetic acid=100:200:1) until disappearance of the starting materials. After completion of the reaction, the reaction solution is dissolved in 20 mL of ethyl acetate, washed respectively with 20 mL of saturated sodium chloride solution and 20 mL of water three times. The ethyl acetate layer is dried over anhydrous magnesium sulphate and then isolated by column chromatography (ethyl acetate:petroleum ether=1:1). Fractions are collected and tested. The collected product is subjected to rotary evaporation under reduced pressure to dryness, resulting in 8.02 mg of a white solid with a yield of 70%. The resulting product is confirmed by MALDI-TOF mass spectrometry analysis to be the expected product.

MALDI-TOF-MS: m/z=760.2 (M+Na)$^+$ (the chemical formula: $C_{35}H_{36}IN_3O_7$, the calculated molecular weight: 737.16).

(4) Synthesis of Compound 4

Compound 3 (11.5 mg, 15.6 mmol) is weighed into a 1 mL EP tube and dissolved in 500 μL of DMF. c(RGDfk) (9.4 mg, 15.6 mmol) is added, followed by addition of DIEA to adjust pH to 8.5. The reaction runs at 30° C. for 2 hrs. The reaction is monitored by HPLC. HPLC (High-performance liquid chromatography) procedure 1: Agilent 1100 Series HPLC system equipped with YMC-Pack ODS-A C18 Semi-Preparative Column (10 mm×250 mm, 120 Å pore size, particle size of 5 μm) is used with a gradient rinsing for 25 minutes and a flow-rate of 1 mL/min, in which the mobile phase A is an aqueous solution and B is acetonitrile (containing 0.05% TFA). The gradient for rinsing is set as follows: 100% A and 0% B at the start, 0% A and 100% B at 20 min, and 100% A and 0% B at 25 min. There is a peak at 14.854 min for the product.

(5) Synthesis of Compound 5

125 µL of piperidine is added into the EP tube in the last step, the Fmoc protective group is deprotected, 500 µL of ethyl ether is added into the reaction system and high-speed centrifugal sedimentation is performed. The ethyl ether phase is discarded and the resulting product is a white solid of about 9.55 mg with a yield of 61%. The resulting product is confirmed by MALDI-TOF mass spectrometry analysis to be the expected product.

MALDI-TOF-MS: m/z $[C_{43}H_{62}IN_{11}O_9]^+$ $(M+H)^+$, 1004.38; the observed value: 1004.88. A small amount of the solid was obtained, weighed, dissolved and identified by HPLC to be of 94.4% purity.

(6) Synthesis of Compound 6

Compound 5 (5 mg, 4.98 mmol) is weighed and 3.79 mg of DOTA-NHS-ester is dissolved in 400 µL of DMF. DIEA is added to adjust pH to be 8.5 and reacted at 30° C. for 30 min with shaking. Isolation and purification by semi-preparative HPLC, HPLC procedure 2: Agilent 1100 Series HPLC system equipped with YMC-Pack ODS-A C18 Semi-Preparative Column (10 mm×250 mm, 120 Å pore size, particle size of 5 µm) is used with a gradient rinsing for 25 minutes and a flow-rate of 1 mL/min, in which the mobile phase A is an aqueous solution and B is acetonitrile (containing 0.05% TFA). The gradient for rinsing is set as follows: 80% A and 20% B at the start, 50% A and 50% B at 20 min, and 80% A and 20% B at 25 min. The fraction with a retention time of 15.7 minutes is collected. The collected liquid is combined and lyophilized, resulting a white powder of 3.2 mg. The yield is 46.3% with a purity of >95%. The resulting product is confirmed by MALDI-TOF mass spectrometry analysis to be the expected product.

MALDI-TOF-MS: m/z $[C_{55}H_{80}IN_{15}O_{16}]^+$ $(M+H)^+$, 1390.50; the observed value: 1390.7040. Purity is identified by HPLC to be 98%.

(7) Preparation, Purification and Quality Control of $^{68}$Ga-DOTA-A-c(RGDfk) DOTA-A-c(RGDfk) is weighed accurately, quantified, re-dissolved with water, aliquoted into 20 µg/tube, and placed into a −80° C. refrigerator for storage. Upon radiolabelling, the aliquoted compound is removed and thawed at room temperature for 30 min.

Preparation: The $^{68}$Ge-$^{68}$Ga generator is rinsed with 0.05 M of HC1, yielding 12.4 mCi (469.9 MBq) of $^{68}$Ga solution. 500 µL of the $^{68}$Ga rinse fluid is measured and placed into a clean EP tube. 12 µL of 1.25 M NaOAc solution is added to adjust the pH value to be 4.0. The $^{68}$Ga fluid (4.0 mCi, 148 MBq) is added into a EP tube containing the polypeptide. The tube is heated with metal bath heating to 100° C. and the reaction runs for 10 min.

Purification: Purification is performed with a small Sep-Pak C-18 column. First, the Sep-Pak C-18 column is activated with 10 mL of absolute ethanol, followed immediately with washing the column with 10 mL of $H_2O$. Then, the radioactive sample is passed through the Sep-Pak C-18 column and the column is washed with 10 mL of normal saline to remove the free $^{68}$Ga. At last, the column is washed with 0.4 mL of 80% ethyl alcohol and the radiolabelled product is collected. The product is sterilized through a 0.22 µm microporous filter membrane and used in the following in vivo experiments.

Quality Control: The radioactive probe is left at room temperature for 10 min and monitored for purity by radio-HPLC. Labeling efficiency and radiochemical purity are determined by radio-HPLC. A HPLC system equipped with an on-line radiation detector and the Zorbax C18 analytical column (4.6 mm×250 mm, 300 Å pore size) is used with a gradient rinsing for 30 minutes and a flow-rate of 1.0 mL/min, in which the mobile phase A is an aqueous solution and the mobile phase B is acetonitrile (containing 0.05% TFA). The gradient for rinsing is set as follows: 100% A and 0% B at the start, 95% A and 5% B at 5 min, 78% A and 22% B at 30 min, and returning to the baseline gradient of 100% A and 0% B at 30-35 minutes.

Figure 1B:
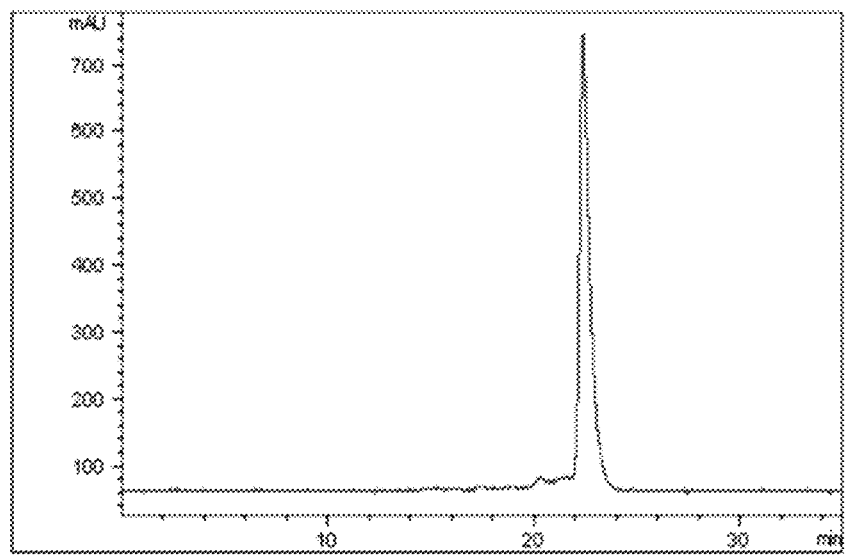

Before labeling, both water and the buffer to be used are treated with Chelex 100 column to remove metallic ions. $^{68}$Ga-DOTA-A-c(RGDfk) is labelled in an one-step process which is a simple and rapid preparation with a labeling efficiency of 85%. After purification on C-18 Sep-Pak column, the radiochemical purities of the labelled products are all greater than 99%. The yield of the labelled product is 80% after correction and calculation, which is shown in FIGS. 1A and 1B.

EXAMPLE 2

The Experiment on the Biodistribution in vivo of the Molecular Probe of Example 1

36 of the tumor-bearing C57BL/6J mice are randomized into nine groups with 4 mice per group. Among the groups, mice in each of the four groups were injected via tail vein with 0.1 mL of $^{68}$Ga-DOTA-A-c(RGDfk) (about 1.85 MBq) and $^{68}$Ga-DOTA-c(RGDfk) (about 1.85 MBq), respectively. The mice were sacrificed after blood collection at 0.5, 1, 2, and 4 h, and dissected to obtain heart, liver, spleen, lung, kidney, intestine, stomach, bone, muscle, and tumor. The mass and the radioactive count of the dissected parts were determined and the dissected parts were weighed and measured for the radiation counting cpm. The percent injected dose per gram tissue (% ID/g) was calculated after decay correction. Mice in the remaining one group were injected simultaneously with 0.1 mL of the $^{68}$Ga-DOTA-A-c(RGDfk) solution and 0.05 mL of the c(RGDfk) (0.5 mg) solution and sacrificed one hour later. Organs were removed and weighed to measure the radiation counting cpm. The percent injected dose per gram tissue (% ID/g) was calculated after decay correction.

Figure 2:
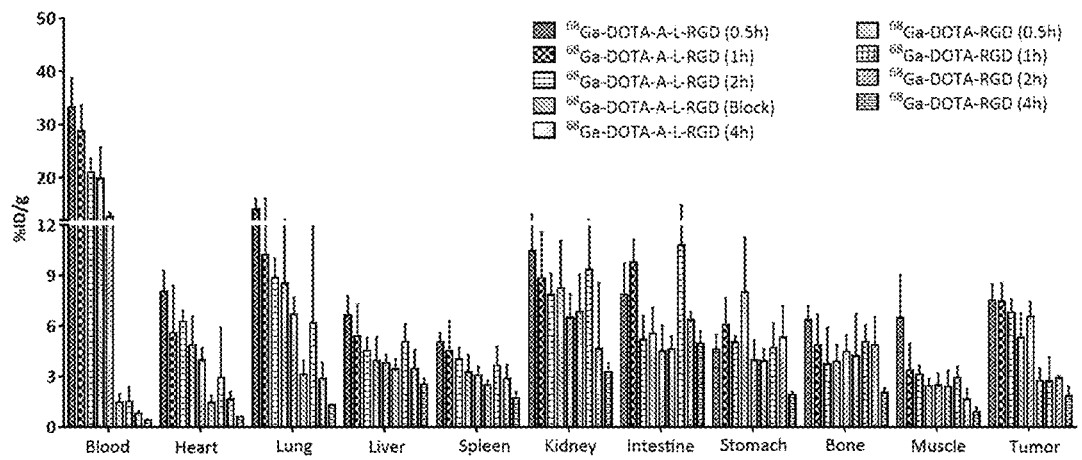
FIG. 2: The biodistribution of the molecular probe and the control probe of Example 1 in the body of the LLC-bearing C57BL/6J mice.

The uptake values of $^{68}$Ga-DOTA-A-c(RGDfk) in blood and in the tumor 0.5 h after injection were 33.32±5.49% ID/g and 7.52±0.99% ID/g, respectively, in comparison with the respective uptake values of $^{68}$Ga-DOTA-c(RGDfk) in blood and in the tumor 0.5 h after injection being 1.49±0.49% ID/g and 2.74 ±0.73% ID/g. In the subsequent time points, the tumor uptakes of $^{68}$Ga-DOTA-A-c(RGDfk) were consistently higher than those of $^{68}$Ga-DOTA-c(RGDfk). The tumor uptake value for $^{68}$Ga-DOTA-A-c(RGDfk) 4 h after injection was 6.57±0.89% ID/g, 3.5 times that of $^{68}$Ga-DOTA-c(RGDfk). The above indicates that the novel probe can binds efficaciously to blood serum proteins, increase the half-life of the probe in blood, and increase efficaciously the tumor uptake value (P<0.01, n=4). The probe is metabolized through kidney. The biodistribution data is shown in FIG. 2.

EXAMPLE 3

Preparation of $^{99m}$Tc-HYNIC-A-3PRGD$_2$

The schematic for the route of synthesizing HYNIC-A-3PRGD$_2$ is as follows:

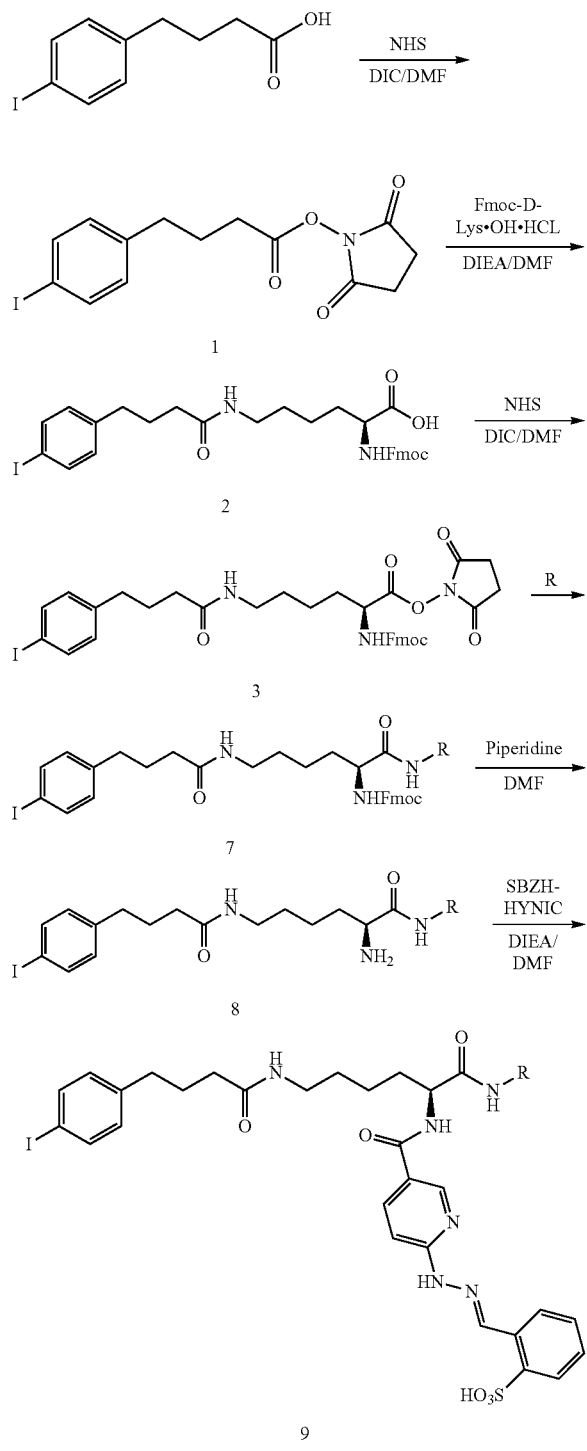

R = 3PRGD$_2$ (1) Synthesis of Compound 1, 2, and 3

Synthesis procedure for the compounds is referred to in Example 1.

(2) Synthesis of Compound 7

Compound 3 (5.64 mg, 7.65 mmol) is weighed into a 1 mL EP tube and dissolved in 500 μL of DMF. 3PRGD$_2$ (15.75 mg, 7.8 mmol) is added, followed by addition of DIEA to adjust pH to 8.5. The reaction runs over night at room temperature. The reaction is monitored by HPLC. With HPLC procedure 1 as mentioned above, there is a peak at 13.17 min for the product. The HPLC fraction is collected and identified by mass spectrometry to be the expected product.

MALDI-TOF-MS: m/z=2680.89 (the chemical formula: $C_{123}H_{181}IN24O_{35}$ and the calculated molecular weight: 2681.22 Da.).

(3) Synthesis of Compound 8

125 μL of piperidine is added into the EP tube in the last step, the Fmoc protective group is deprotected, 500 μL of ethyl ether is added further into the reaction system and high-speed centrifugal sedimentation is performed. The ethyl ether phase is discarded and the resulting product is a white solid of about 10.6 mg with a yield of 56%. The resulting product is confirmed by MALDI-TOF mass spectrometry analysis to be the expected product.

MALDI-TOF-MS: m/z=2460.85 (M+H)$^+$, 2482.87 (M+Na)$^+$ (the chemical formula: $C_{108}H_{171}IN_{24}O_{33}$ and the calculated molecular weight: 2459.15 Da.).

A small amount of the solid was obtained, weighed, re-dissolved and assayed for purity by HPLC with the purity of 92.5%

(4) Synthesis of Compound 9

Compound 8 (5 mg, 2.03 mmol) is weighed and 0.9 mg of SBZH-HYNI is dissolved in 500 μL of DMF. DIEA is added to adjust pH to be 8.5 and reacted at 30° C. for 10 min with shaking. Isolation and purification by semi-preparative HPLC, HPLC procedure 3: Agilent 1100 Series HPLC system equipped with YMC-Pack ODS-A Semi-Preparative Column (10 mm×250 mm, 120 Å pore size, particle size of 5 μm) is used with a gradient rinsing for 30 minutes and a flow-rate of 1 mL/min, in which the mobile phase A is an aqueous solution and the mobile phase B is acetonitrile (containing 0.05% TFA). The gradient for rinsing is set as follows: 100% A and 0% B at the start, 75% A and 25% B at 5 min, 50% A and 50% B at 25 min, and returning to the baseline gradient of 100% A and 0% B at 25-30 minutes. The fraction with a retention time of 15.2 minutes is collected. The collected liquid is combined and lyophilized, resulting a white powder of 1.95 mg. The yield is 34.8% with a purity of >95%. The resulting product is confirmed by MALDI-TOF mass spectrometry analysis to be the expected product.

MALDI-TOF-MS: m/z=2763.07 (M+H)$^+$, 2785.21 (M+Na)$^+$ (the chemical formula: $C_{121}H_{180}IN_{27}O_{37}S$ and the calculated molecular weight: 2762.18 Da.).

A small amount of the solid was obtained, dissolved and assayed by HPLC to be of more than 99% purity.

(5) Preparation and Quality Control of $^{99m}$Tc-HYNIC-A-3PRGD$_2$

20 μL of HYNIC-A-3PRGD$_2$ (1 mg/mL, dissolved in pure water), 100 μL of tricine solution (100 mg/mL, dissolved in 25 mM succinate buffer, pH 5.0), 100 μL of TPPTS (60 mg/mL, dissolved in 25 mM succinate buffer, pH 5.0), and 100 μL of Na$^{99m}$TcO$_4$ (10 mCi) were added into an EP tube sequentially. The resulting mixture was mixed to homogeneity and then heated in a water bath at 100° C. for 25 min. The labelled product was cooled and assayed for labeling efficiency and radiochemical purity by HPLC (HP 1100 high-performance liquid chromatography, equipped with LB-509 radiation detector).

Figure 3:
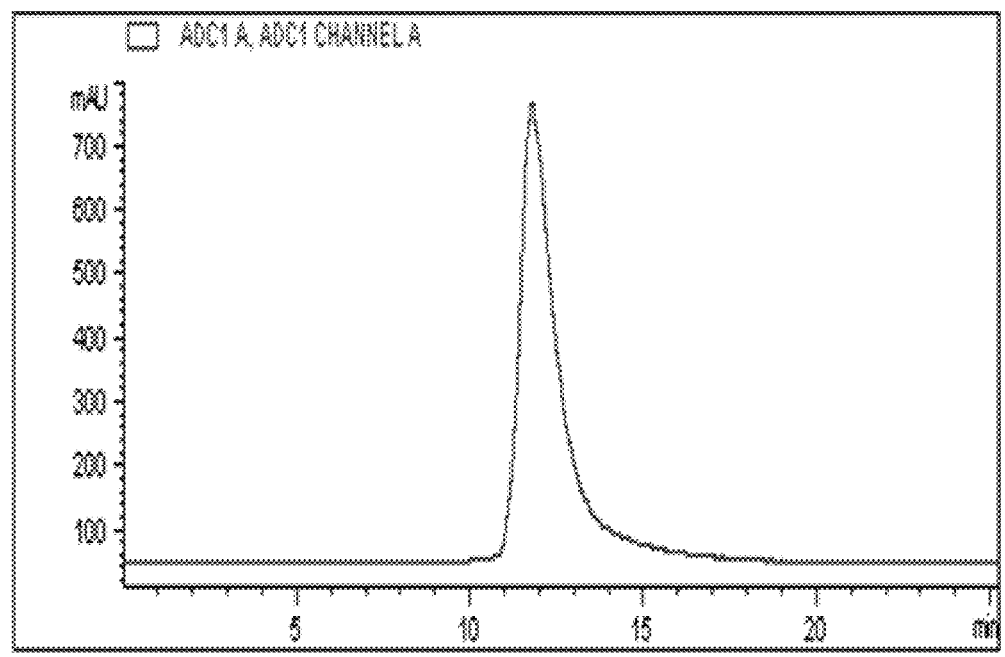
FIG. 3: The chromatogram of radio-HPLC for $^{99m}$Tc-HYNIC-A-3PRGD$_2$, the final product of Example 3.

$^{99m}$Tc-HYNIC-A-3PRGD$_2$ was prepared by a non-SnCl$_2$ one-step procedure. The labelled product was assayed by the radio-HPLC with the retention time of $^{99m}$Tc-HYNIC-A-3PRGD$_2$ being 11.8 min and the measured labeling efficiency of >99%. The results are shown in FIG. 3.

EXAMPLE 4

Blood Clearance Experiment on the Molecular Probe of Example 3

14 of KunMing female mice aged 4-5 weeks were obtained and randomized into two groups. Mice in each of the groups were injected with 0.1 mL of $^{99m}$Tc-HYNIC-A-3PRGD$_2$ and $^{99m}$Tc-HYNIC-3PRGD$_2$ (individually about 1.85 MBq), respectively. Blood was collected at 1, 3, 5, 7, 10, 15, 20, 30, 60, 90, 120 min after injection and the radiation counting cpm was measured. The percent injected doses per gram (% ID/g) for the two probes in blood were calculated after decay correction.

Figure 4:
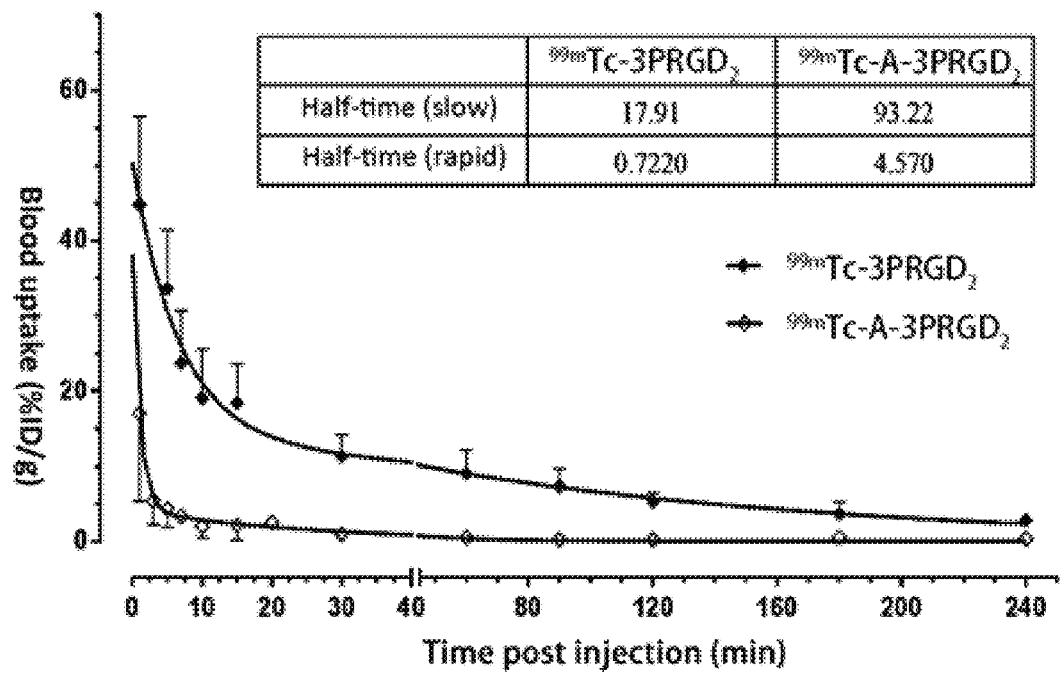
FIG. 4: Graph for the result of the blood clearance experiment in Example 3.

By the blood clearance experiment, we can see that the properties of the structurally modified 3PRGD$_2$ probe in the body were changed significantly in comparison to those of the original probe. The drug rapid and slow half-lives of $^{99m}$Tc-HYNIC-A-3PRGD$_2$ were 4.57 and 93.32 min, respectively. However, the drug rapid and slow half-lives of $^{99m}$Tc-HYNIC-3PRGD$_2$ (not structurally modified) were 0.72 and 17.91 min, respectively. The drug rapid and slow half-lives were increased by 6.3- and 5.2-fold, respectively. At 1 min of the injection, the uptake value in blood was 17.07±11.77% ID/g for the unmodified molecular probe, and 44.76±11.83% ID/g for $^{99m}$Tc-HYNIC-A-3PRGD$_2$, the latter being 2.6-fold the former. At 5 min, the uptake value was only 4.39±2.55% ID/g for the former, and 33.63±7.83% ID/g for the latter (namely, the molecular probe of the invention), the latter being 7.6-fold the former. At 10 min, the uptake value was 1.99±1.54% ID/g for the former, and 19.06±6.51 20% ID/g for the latter. The uptake value for the former was decreased below 0.5% ID/g at 60 min after injection, and was 0.34±0.18% ID/g at 240 min vs that for the latter being 2.81±0.83% ID/g and 8-fold that for the original probe. It can be seen that the structural modification extends the blood residence time of 3PRGD$_2$ much longer (P<0.01, n=7), which is favorable for the increased uptake value of the probe at tumor site. The result of the blood clearance experiment is shown in FIG. 4.

EXAMPLE 5

SPECT/CT Imaging of the Tumor-Bearing Nude Mice with the Molecular Probe of Example 3

Figure 5:
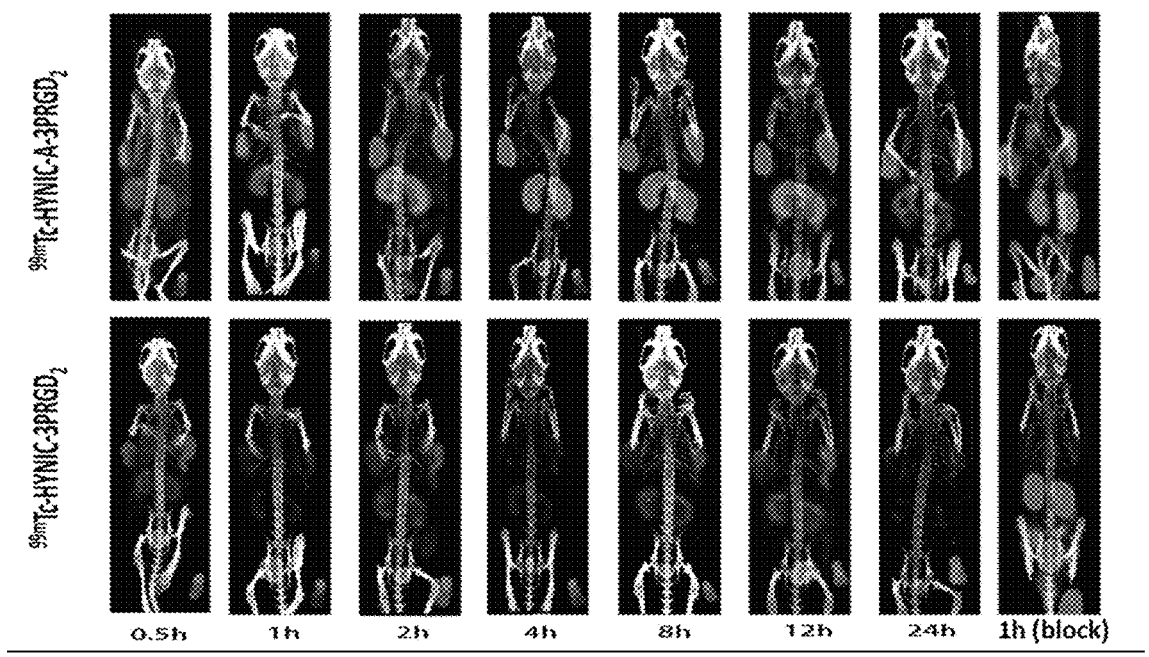
FIG. 5: Pictures for SPECT/CT imaging the U87 MG-bearing nude mice in Example 3.

$^{99m}$Tc-HYNIC-A-3PRGD$_2$ (hereinafter referred to as the molecular probe of the invention) was prepared according to Example 3. At the same time, $^{99m}$Tc-HYNIC-3PRGD$_2$ (hereinafter referred to as the control probe) was prepared according to the labeling procedure for 3PRGD$_2$. After being detected by radio-HPLC, each of the probes were diluted with normal saline to 2 mCi/100 µL and the dilutions were injected intravenously into the U87-MG tumor-bearing nude mice. Each of the mice were injected via tail vain with 100 µL of $^{99m}$Tc-HYNIC-A-3PRGD$_2$. The specific uptaking of the agent into various organs and tissues of the tumor-bearing mice was validated by the blockade experiment. Mice in the blockade group were injected via tail vain with 100 µL of 1 mg 3PRGD$_2$ cold peptide, followed immediately by injection with 100 L, of $^{99m}$Tc-HYNIC-A-3PRGD$_2$. At the same time, each of the agents was measured in 50 µCi and quantified. The SPECT/CT images were acquire at 0.5, 1, 2, 4, 8, 12, and 24 hours after injection, respectively. Pictures of SPECT/CT imaging U87 MG-bearing nude mice are shown in FIG. 5.

Figure 6A:
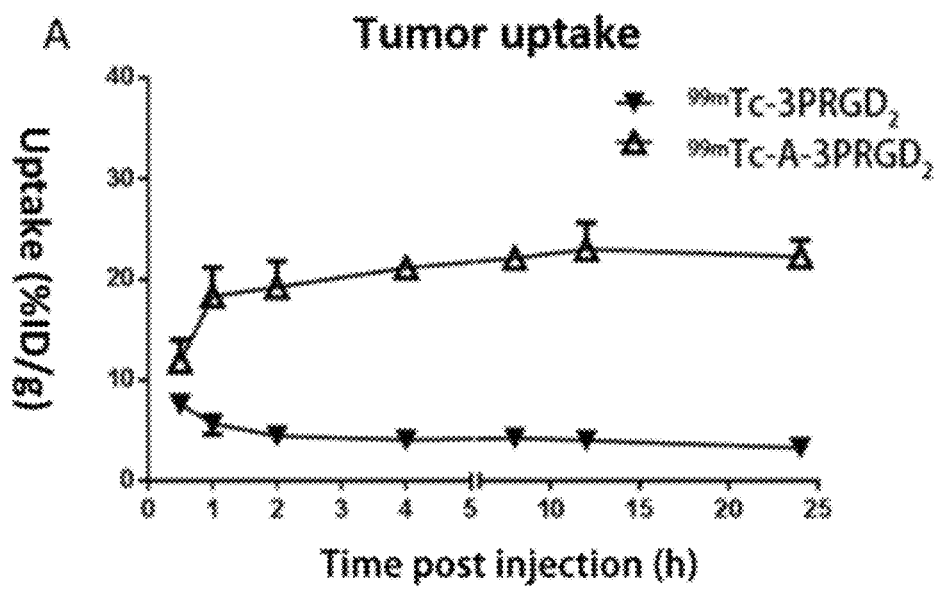
FIGS. 6A-6D: The comparison chart of the % Dig in U87 tumor, the tumor/kidney, tumor/muscle, and tumor/liver ratios of the inventive and control probes in the SPECT/CT imaging result of Example 3.
Figure 6B:
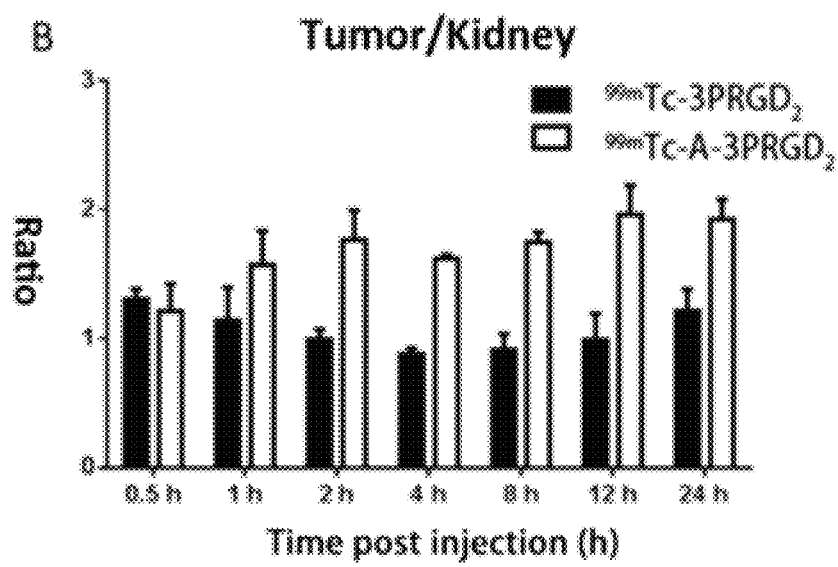
Figure 6C:
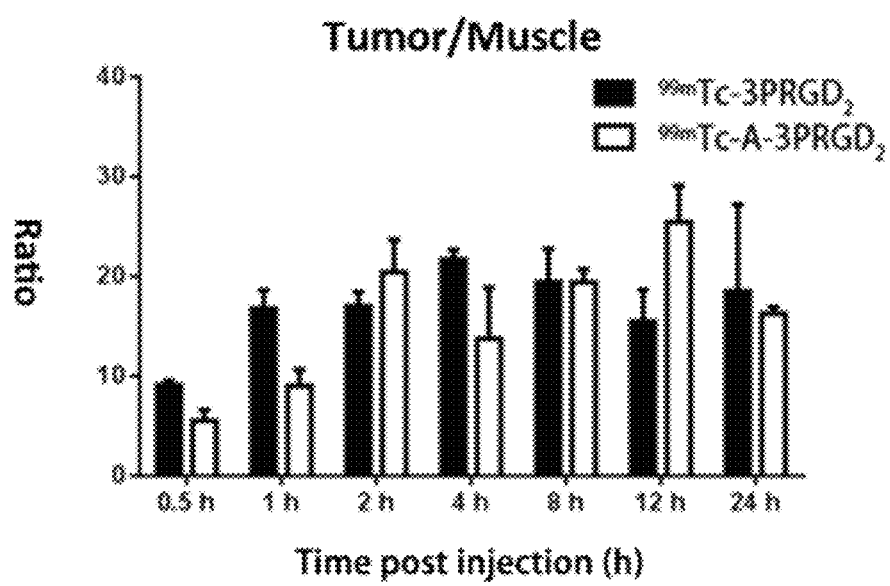
Figure 6D:
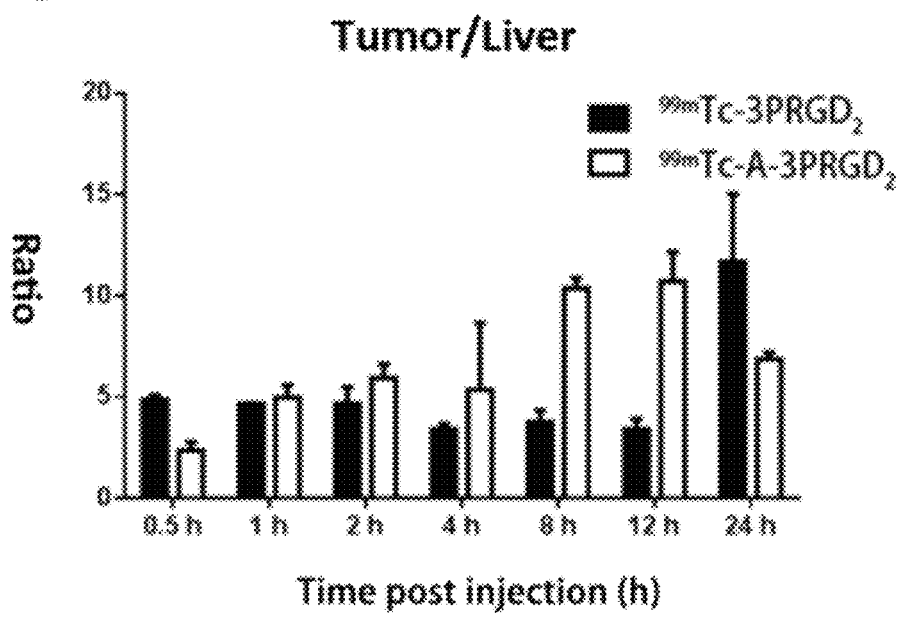

FIG. 6A is the % ID/g of $^{99m}$Tc-HYNIC-A-3PRGD$_2$ and $^{99m}$Tc-HYNIC-3PRGD$_2$ in the U87 tumor; FIGS. 6B, 6C and 6D are comparison of the tumor/kidney, tumor/muscle, and tumor/liver ratios of $^{99m}$Tc-HYNIC-A-3PRGD$_2$ and $^{99m}$Tc-HYNIC-3PRGD$_2$, respectively. The result is expressed as the mean±SD (n=3).

The tumor was imaged very well with the molecular probe of the invention at each of the acquisition time points, even at 24-hour after injection. This is related to the longer blood residence time of the modified probe, therefor the enhanced tumor uptake. As shown in the quantitative analysis in FIG. 6A, the molecular probe of the invention is cleared very slowly at the tumor, with 11.85±2.18% ID/g, 21.17±0.49% ID/g, and 22.27±1.64% ID/g at 0.5, 8, and 24 h after injection, respectively. As shown in FIG. 6B, the tumor/kidney ratios of the modified novel probe are increased in comparison with the control probe. The tumor/kidney ratio of the control probe is 1.14±0.26 1 hour after injection and 1.21±0.17 24 hours after injection with the corresponding ratios of the molecular probe of the invention being 1.57±0.26 and 1.92±0.17, respectively. The tumor/non-tumor ratio of the modified 3PRGD$_2$ is improved as well, as shown in FIGS. 6C and 6D. This indicates that the biodistribution property and the pharmacokinetic profile of the modified molecular probe is better than those of the original probe.

EXAMPLE 6

Biodistribution of the Molecular Probe of Example 3

24 of the U87-bearing nude mice were randomized into 6 groups with 4 mice per group. Time points were set at 1, 2, 4, 8, and 12 hours. Nude mice in each group were injected via tail vein with 20 µCi of $^{99m}$Tc-HYNIC-A-3PRGD$_2$. A group of the nude mice injected with 3PRGD$_2$ were used as the blockage group. The animals were sacrificed after the injection. Blood and main viscera were removed, weighed, and measured for radiation counting cpm. The percent injected doses per gram (% ID/g) was after decay correction.

Preparation of the reference sample for biodistribution: 100 µL of the solution of the label to be used in the biodistribution experiment was added with a injector into a volumetric flask of 100 mL and water was added to make up to volume of 100 mL and thoroughly mixed. 1 mL of the resulting solution was obtained accurately with a pipetted and measured with a gamma counter for radiation counting. This radiation counting is scaled-up 100-fold serving as a Standard injection dose for injection. Three parallel samples were prepared and the average value was obtained from the parallel samples.

Figure 7:
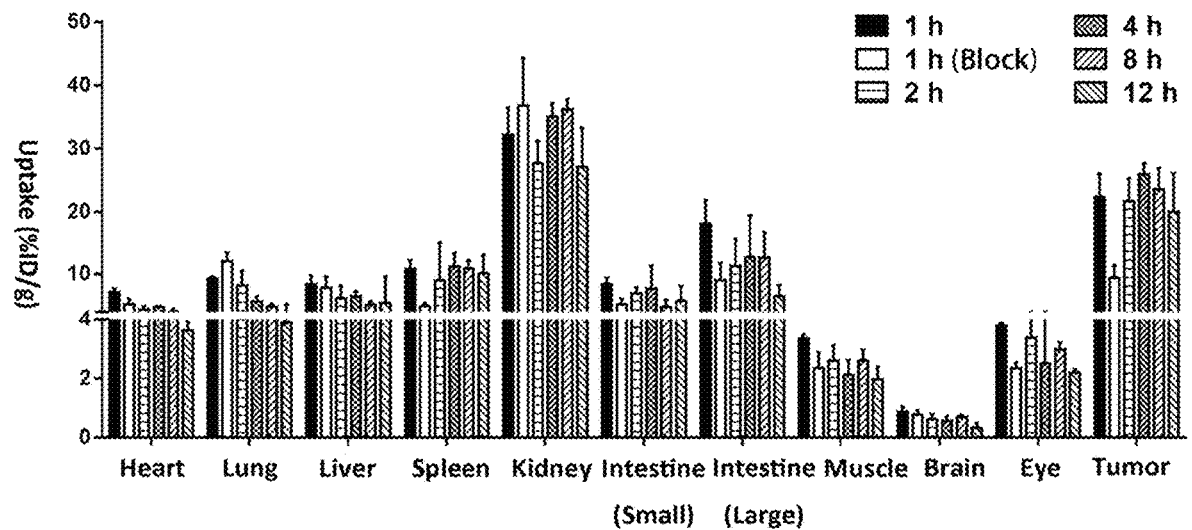
FIG. 7: The distribution of the molecular probe of Example 3 in the body of the U87 MG-bearing nude mice.

As shown in FIG. 7, after injection with $^{99m}$Tc-HYNIC-A-3PRGD$_2$ via tail vain, the uptake of the imaging agent in U87 tumor was increased first and then decreased over the extended time. The uptakes in the tumor at the four time points of 1, 2, 4, and 8 h were shown respectively as follows: 22.38±3.68% ID/g, 21.71±3.61% ID/g, 25.96±1.69% ID/g, 23.53±3.40% ID/g. The organ with the highest uptake is kidney in which ID/g was consistently above 30% % ID/g. So the radioactive probe should have been metabolized through the kidney, which is consistent with the SPECT/CT imaging result. The uptakes of the probe in the remainder of the organs after injection are higher than those of the control probe, for structural modification on the polypeptide of the invention enables the polypeptide to circulate together with blood in the body longer time, therefor resulting the variably increased uptake values in all of the organs.

EXAMPLE 7

Preparation of $^{177}$Lu-DOTA-A-L-3PRGD$_2$

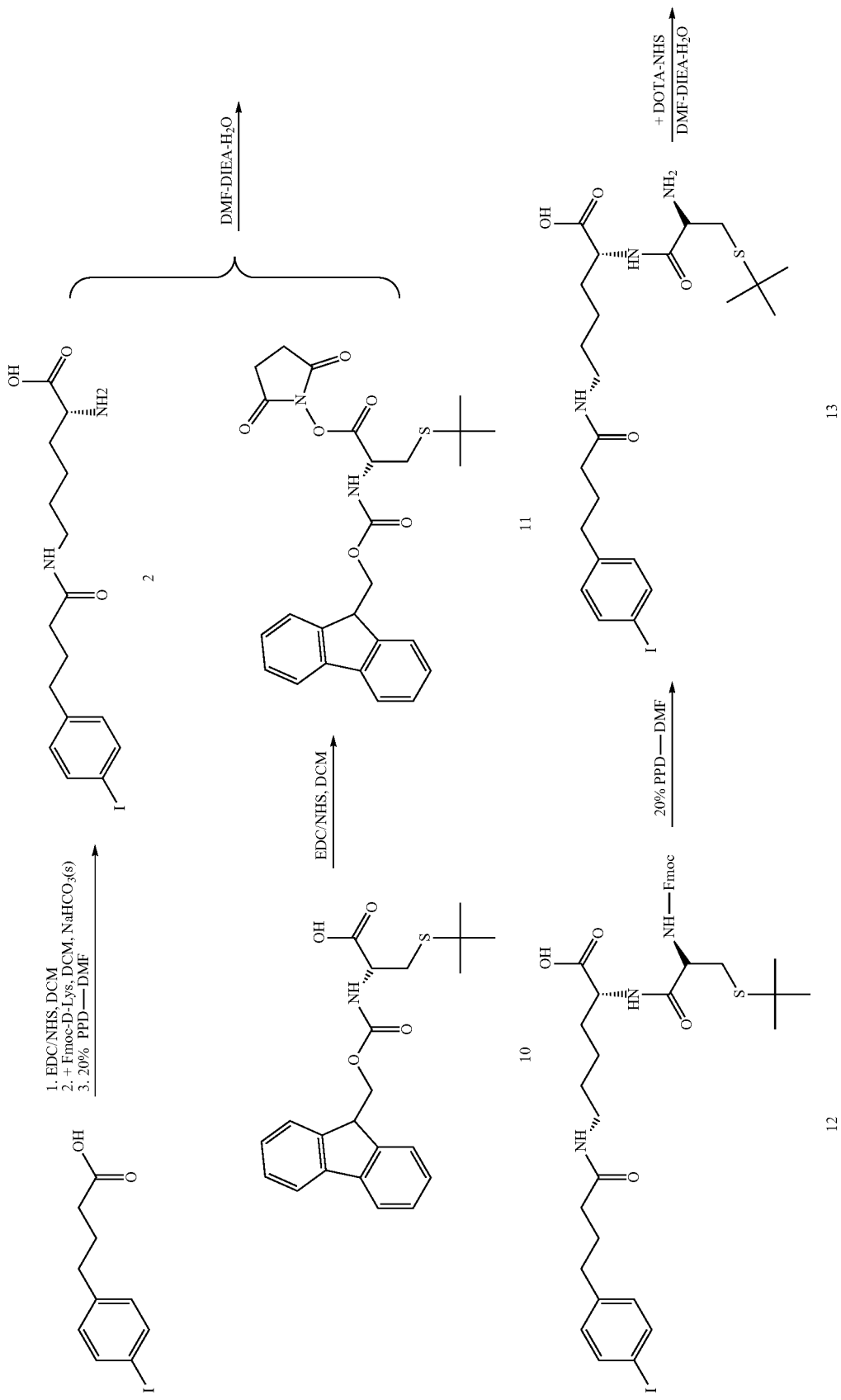

-continued
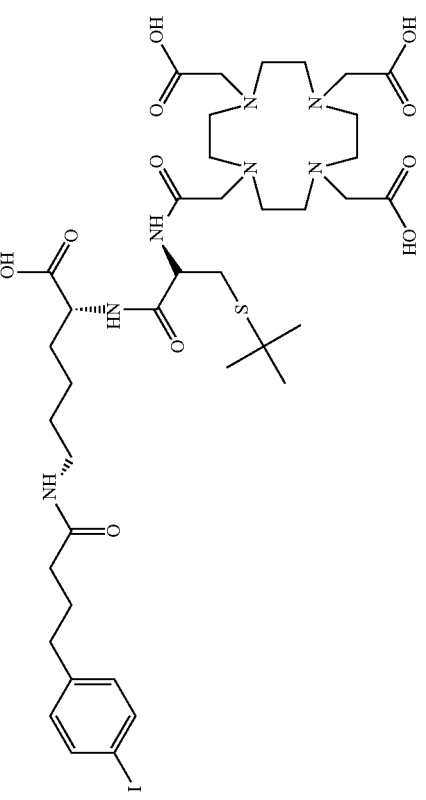
14
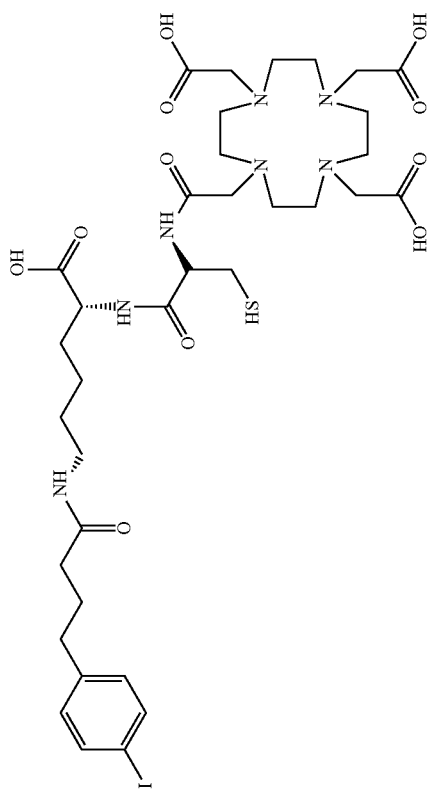
15
20% TFMSA-TFA →
+3PRGD2 / DMF-DIEA →
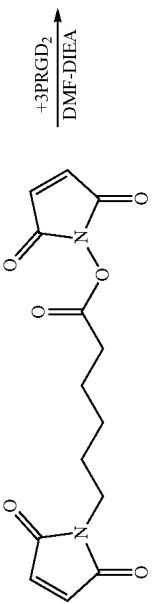

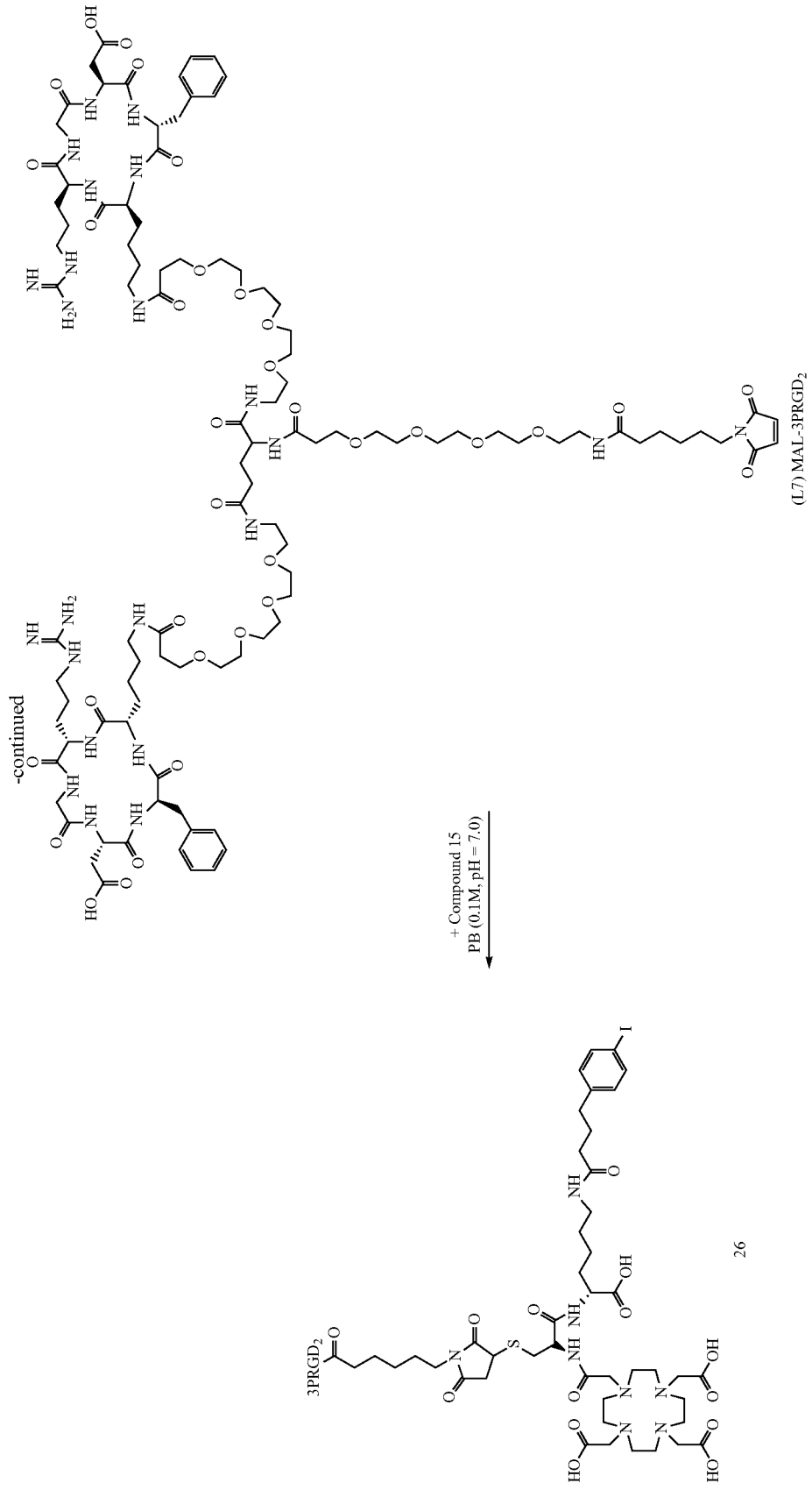

(1) Preparation of Compound 2 is the Same as Example 1

(2) Preparation of Compound 11

100.0 mg (250 μmol) of Compound 10, 76.4 mg (400 μmol) of EDC.HCL and 46.0 mg (400 μmol) of NHS were weighed and dissolved in 5 mL of methylene chloride. The resulting mixture was stirred overnight at room temperature. The mixture was isolated and purified by silica-gel chromatography and the eluent was methylene chloride containing 2% of methanol. The solvent was removed by distillation under the reduced pressure, yielding a white powdery solid of 85.2 mg. The gradient and the time for HPLC procedure were: 50% mobile phase A and 50% mobile phase B at 0 min; 10% mobile phase A and 90% mobile phase B at 25 min; and 50% mobile phase A and 50% mobile phase B at 30 min. A small amount of the product was obtained, tested by HPLC for purity (with the retention time of 17.7 minutes) and then identified by MALDI-TOF mass spectrometry.

(3) Preparation of Compound 12

85.2 mg (147 μmol) of Fmoc-Cys(tBu)-NHS Compound 11 and 61.0 mg (145 μmol) of Compound 2 was weighed. 400 μL of DMF and 20 μL of DIEA were added. The resulting mixture was sonicated in water bath to form a suspension. 400 μL of pure water was added to dissolve totally the solid in the suspension. The resulting solution was stirred at room temperature over night. The mixture was isolated and purified by HPLC. The eluted peak with a retention time of 20.9 min was collected. The gradient and the time for HPLC procedure were: 50% mobile phase A and 50% mobile phase B at 0 min; 10% mobile phase A and 90% mobile phase B at 25 min; and 50% mobile phase A and 50% mobile phase B at 30 min. The collected fraction was lyophilized, yielding a white powdery solid of 67.2 mg. A small amount of the product was obtained, verified by HPLC for purity and then identified by MALDI-TOF mass spectrometry.

(4) Preparation of Compound 13

67.2 mg (84.1 μmol) of Compound 12 was weighed, added into 20% piperidine-DMF, dissolved and then reacted at room temperature for 10 min. The mixture was isolated and purified by HPLC. The eluted peak with a retention time of 24.1 min was collected. The gradient and the time for HPLC procedure were: 85% mobile phase A and 15% mobile phase B at 0 min; 45% mobile phase A and 55% mobile phase B at 25 min; and 85% mobile phase A and 15% mobile phase B at 30 min. The collected fraction was lyophilized, yielding a white powdery solid of 27.8 mg. A small amount of the product was obtained, verified by HPLC for purity and then identified by MALDI-TOF mass spectrometry.

(5) Preparation of Compound 14

10.0 mg (12.5 μmol) of Compound 13 and 10 mg (13.1 μmol) of DOTA-NHS were weighed and dissolved in 200 μL of DMF. 10 μL of DIEA was added. The insoluble was sonicated into a suspension. 200 μL of pure water was added to dissolve totally the solid in the suspension. The resulting solution was stirred at room temperature over night. The mixture was isolated and purified by HPLC. The eluted peak with a retention time of 21.7 min is collected. The gradient and the time for HPLC procedure were: 85% mobile phase A and 15% mobile phase B at 0 min; 45% mobile phase A and 55% mobile phase B at 25 min; and 85% mobile phase A and 15% mobile phase B at 30 min. The collected fraction was lyophilized, yielding a white powdery solid of 8.5 mg. The product was verified by HPLC for purity and then identified by MALDI-TOF mass spectrometry.

(6) Preparation of Compound 15

8.5 mg (8.8 μmol) of Compound 14 was weighed and added into 200 μL of 20% TFMSA-TFA to react for 30 seconds, immediately followed by addition of 400 μL of DMF to prevent acidolysis of the product. The mixture was isolated and purified by HPLC. The eluted peak with the retention times of 26.6 and 26.9 min is collected. The gradient and the time for HPLC procedure were: 85% mobile phase A and 15% mobile phase B at 0 min; 45% mobile phase A and 55% mobile phase B at 25 min; and 85% mobile phase A and 15% mobile phase B at 30 min. The collected fraction was lyophilized, yielding a white powdery solid of 1.2 mg. The product was verified by HPLC for purity and then identified by MALDI-TOF mass spectrometry.

(7) Preparation of MAL-3PRGD$_2$ (L7)

10 mg (4.8 μmol) of 3PRGD$_2$ and 2.0 mg (6.5 μmol) of Mal-NHS were weighed and 200 μL DMF and 10 μL DIEA were added. The mixture liquid was stirred overnight at room temperature. The mixture was isolated and purified by HPLC. The eluted peak with a retention time of 22.1 min is collected. The gradient and the time for HPLC procedure were: 90% mobile phase A and 10% mobile phase B at 0 min; 60% mobile phase A and 40% mobile phase B at 25 min; and 90% mobile phase A and 10% mobile phase B at 30 min. The liquid was lyophilized, yielding a white powdery solid of 6.7 mg. A small amount of the product was obtained, verified by HPLC for purity and then identified by MALDI-TOF mass spectrometry.

(8) Preparation of Compound 16

0.7 mg (0.8 μmol) of Compound 15 was weighed, 1.8 mg (0.8 μmol) of MAL-3PRGD$_2$ was added, and 0.1 M of phosphate buffer (pH=7.0) was added. The reaction run overnight at room temperature with shanking. The product is isolated and purified by HPLC. The eluted peak with a retention time of 25.6 min is collected. The gradient and the time for HPLC procedure were: 90% mobile phase A and 10% mobile phase B at 0 min; 60% mobile phase A and 40% mobile phase B at min; and 90% mobile phase A and 10% mobile phase B at 30 min. The eluents for the product peak were combined and lyophilized, yielding a white powdery solid of 1.2 mg. A small amount of the product was obtained, tested by HPLC for purity and then identified by MALDI-TOF mass spectrometry. Purity of the product was assayed by HPLC to be >98%. The result of MALDI-TOF mass spectrometry was shown to be m/z=3160.84. The experimental result indicates that [M+H]$^+$ is consistent with the theory molecular mass (M=3161,36) of C137H215IN30O45S.

(9) Preparation, Purification and Quality Control of $^{177}$Lu-DOTA-A-L-3PRGD$_2$ 20 μg of Compound 16, DOTA-3PRGD$_2$ or DOTA-A-L was added, then 200 μL of ammonium acetate buffer (0.1 M, pH=4.8) and 5 to 25 mCi $^{177}$LuC13 were added. The mixture liquid was left in air-bath heater at 99° C. and reacted for 20 minutes. The product was yielded after free cooling. To prevent the labelled product from radiation self-decomposition, 200 μL of the aqueous solution of gentisic acid was added (1 mg/mL). The labelled product can be kept stably at room temperature for over 6 hrs.

The radiochemical purity (RCP) of $^{177}$Lu-DOTA-A-L-3PRGD$_2$, $^{177L}$u-3PRGD$_2$ and $^{177}$Lu-DOTA-A-L were determined with HPLC-1260 Infinity Liquid Chromatography System equipped with a radiation detector, the Agilent ZORBAX Extend-C18 (250×4.6 mm, 5 μm) Chromatographic Column (250×10 mm, 5 μm) and a flow rate of 1 mL/min. Mobile phase A is water (containing 0.05% TFA)

and mobile phase B is acetonitrile (containing 0.05% TFA). The gradient and the time for the procedure were: 90% mobile phase A and 10% mobile phase B at 0 to 5 min; 60% mobile phase A and 40% mobile phase B at 25 min; and 90% mobile phase A and 10% mobile phase B at 30 min.

Figure 8:
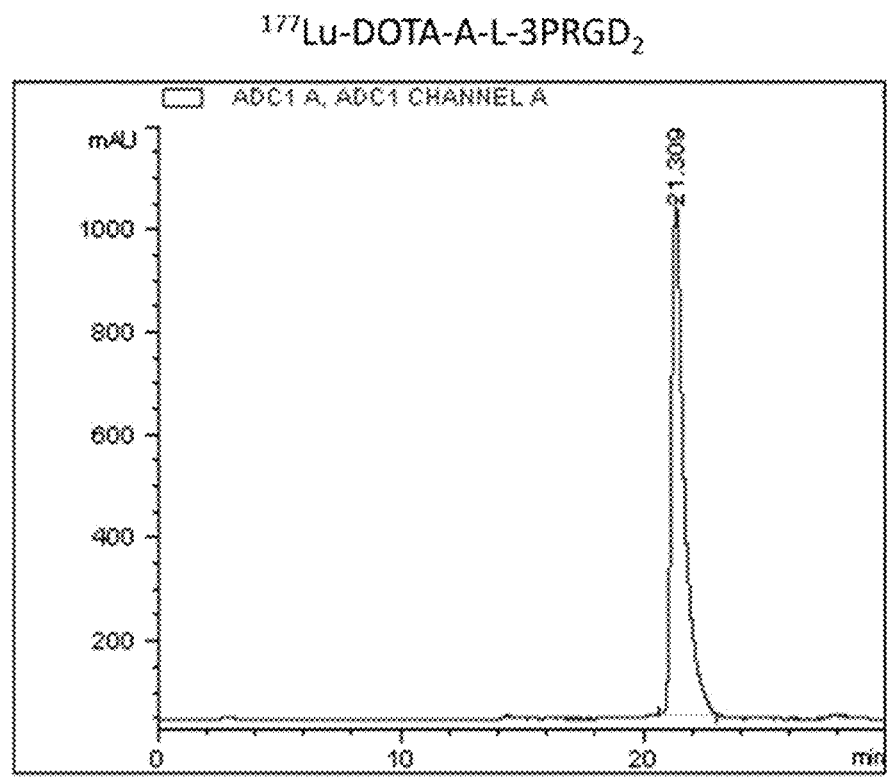
FIG. 8: The chromatogram of radio-HPLC for $^{177}$Lu-DOTA-A-L-3PRGD$_2$, the final product of Example 7.

The chromatogram of radio-HPLC for the final product $^{177}$Lu-DOTA-A-L-3PRGD$_2$ is shown in FIG. 8.

EXAMPLE 8

Distribution of the Molecular Probe of Example 7 in Blood 15 of KunMing mice were randomized into three groups (n=5). The mice were injected individually via tail vein with 100 μL (740 KBq) of $^{177}$Lu-DOTA-A-L-3PRGD$_2$ in Example 14 of the invention and of $^{177}$Lu-3PRGD$_2$ or $^{177}$Lu-DOTA-A-L as a control. An appropriate amount of blood was collected from the medial canthus of the mice after injection, weighed and measured for radiation counting cpm. The percent injected dose per gram tissue (% ID/g) of the radiopharmaceuticals in blood were calculated. Non-linear regression analysis was performed on the experimental results with GraphPad Prism 7.0 software and the rapid and slow half-lives in the two-compartmental model of metabolism in blood (Two phase decay) were calculated.

Figure 9:
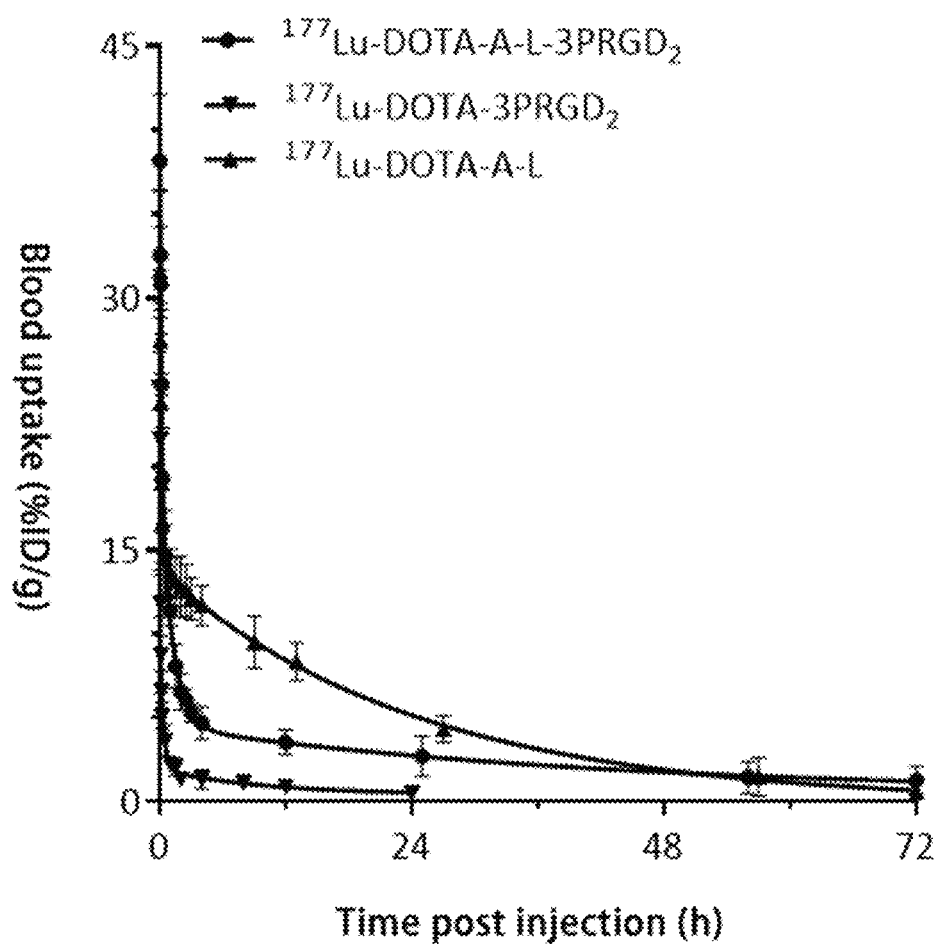
FIG. 9: Graph for the results of the blood clearance experiment on the molecular probe of Example 7.

According to the experimental results shown in FIG. 9, the rapid and slow half-lives for $^{177}$Lu-DOTA-A-L-3PRGD$_2$ are 6.909 min and 77.15 min, respectively, while 1.231 min and 20.83 min for $^{177}$Lu-3PRGD$_2$. It can be seen that blood residence time of $^{177}$Lu-DOTA-A-L-3PRGD$_2$ of the invention is significantly longer than that of $^{177}$Lu-3PRGD$_2$, which turns out that the structural modification on the polypeptide the present invention can extend the residence time of c(RGDfk) in blood indeed. This indicates that the RGD probe adapted in the present invention binds strongly to MSA and can be circulated together with blood in the body longer, resulting in the increased concentration of the radioactive probe in blood. The integral of the percent injected dose per gram tissue (% ID/g) of the probe in blood with respect to time (area under the curve, AUC) can exhibit the effect of the agent in blood. AUCs (% ID/g-h) of $^{177}$Lu-DOTA-A-L-3PRGD$_2$, $^{177}$Lu-3PRGD$_2$ 0 to 72 hours after administration is sequentially 208.9 and 27.0. The experimental result indicates that the blood pharmacokinetic of the novel $^{177}$Lu-DOTA-A-L-3PRGD$_2$ of the invention in blood is 7.7 times higher than that of $^{177}$Lu-3PRGD$_2$. While the shortest low half-life of $^{177}$Lu-DOTA-A-L in blood is longer than that of the molecular probe of the invention, the other properties thereof as a molecular probe are inferior much to those of the molecular probe of the invention, such as residence and uptake in the tumor, which will be detailed in the following Examples.

EXAMPLE 9

SPECT/CT Imaging of the Tumor-Bearing Nude Mice with the Molecular Probe of Example 7

Figure 10:
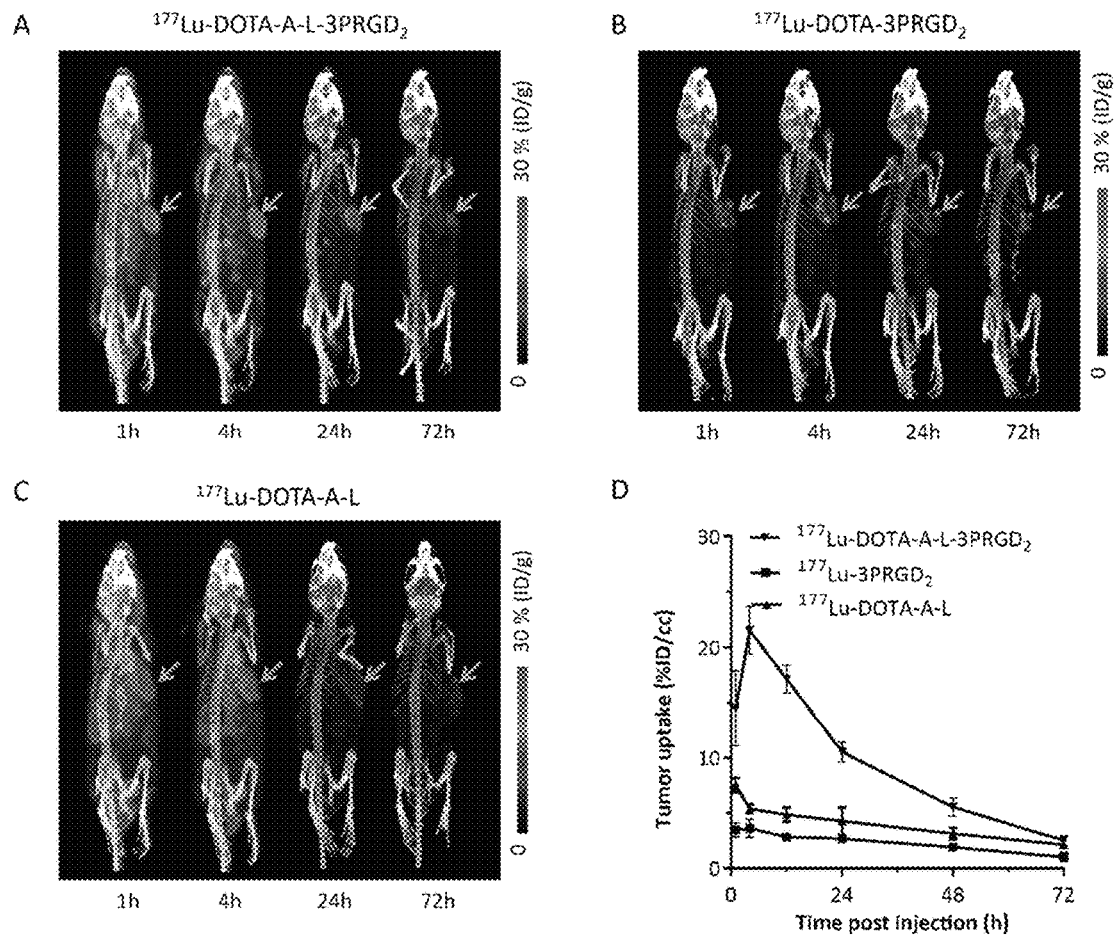
FIG. 10: Graphs for SPECT/CT imaging the U87 MG-bearing nude mice with the molecular probe of Example 7.

The SPECT/CT imaging system (Mediso) has 4 probes and parallel hole collimators. The U87-MG tumor-bearing mice were injected via the tail vein with 100 μL (20 MBq) of $^{177}$Lu-DOTA-A-L-3PRGD$_2$, $^{177}$Lu-3PRGD$_2$, or $^{177}$Lu-DOTA-A-L. Then, SPECT imaging was performed 1, 4, 8, 12, 24, 48 and 72 hr. after injection. Mice were anesthetized with 1.5% isoflurane-oxygen mixture during imaging and restrained in prone position on a small animal bed. Mice in the blockade group were injected with the labelled product mixed simultaneously with 1.0 mg of 3PRGD$_2$ cold peptide. The SPECT image and the CT image were merged and the region of interest (ROI) in the SPECT image was outlined in the 3D image. The percent injected dose per gram of tissue and organ (% ID/cc) was calculated. The imaging and quantification results include the physical and biological half-life, with no decay correction. The results were shown in FIG. 10.

We find that the probe of the invention $^{177}$Lu-DOTA-A-L-3PRGD$_2$ has an appropriate pharmacokinetics, a high tumor uptake and a high tumor contrast in the tumor. More importantly, the uptake of the probe in the tumor is consistently higher than those thereof in all of the other normal tissues and organs. Quantification of the tumor in the tumor-bearing mice 1 to 72 hours after injection indicated that the accumulative uptake values for $^{177}$Lu-DOTA-A-L-3PRGD$_2$, $^{177}$Lu-3PRGD$_2$, and $^{177}$Lu-DOTA-A-L in the tumor were 662.0, 158.7, and 266.3 ID/cc-h, respectively. The tumor was imaged very well with $^{177}$Lu-DOTA-A-L-3PRGD$_2$ at each of the acquisition time points, and imaged sharply at tumor site even 48 hours after injection, while the control probe exhibited a high background, a low contrast ratio and few enrichment at the tumor site. As shown by the quantitative analysis in FIG. 10, the molecular probe of the invention exhibited the highest uptake value at the tumor and was cleared very slowly. The tumor uptake was highest 4 hour after administration in the tumor-bearing mice with the percent injected doses per gram of 26.52±0.58% ID/g. It indicates that the biodistribution property and the pharmacokinetic profile of the molecular probe of the invention is better than those of the original probe.

EXAMPLE 10

The Experiment on the Biodistribution of the Molecular Probe of Example 7 in the Body Sixteen of the U87-MG tumor-bearing mice were injected via the tail vein with 100 μL (0.74 MBq) of $^{177}$Lu-DOTA-A-L-3PRGD$_2$, (n=4). The mice were sacrificed 1, 4, 24 and 72 hrs. after injection 0.4 of the tumor-bearing mice were obtained and injected via tail vein with 100 μL of the mixture of 740 KBq of $^{177}$Lu-DOTA-A-L-3PRGD$_2$ and 0.5 mg of 3PRGD$_2$ cold peptide. The mice were sacrificed 1 hour after injection. 12 of the tumor-bearing mice were obtained and randomized into 3 groups (n=4) and injected via tail vein with 100 μL (0.74 MBq) of $^{177}$Lu-DOTA-A-L-3PRGD$_2$, $^{177}$Lu-3PRGD$_2$ or $^{177}$Lu-DOTA-A-L and sacrificed 4 hour after injection. Blood and other main tissues and organs were removed, weighed and measured for the radiation counting (cpm). The percent injected dose per gram tissue (% ID/g) was calculated.

Figure 11A:
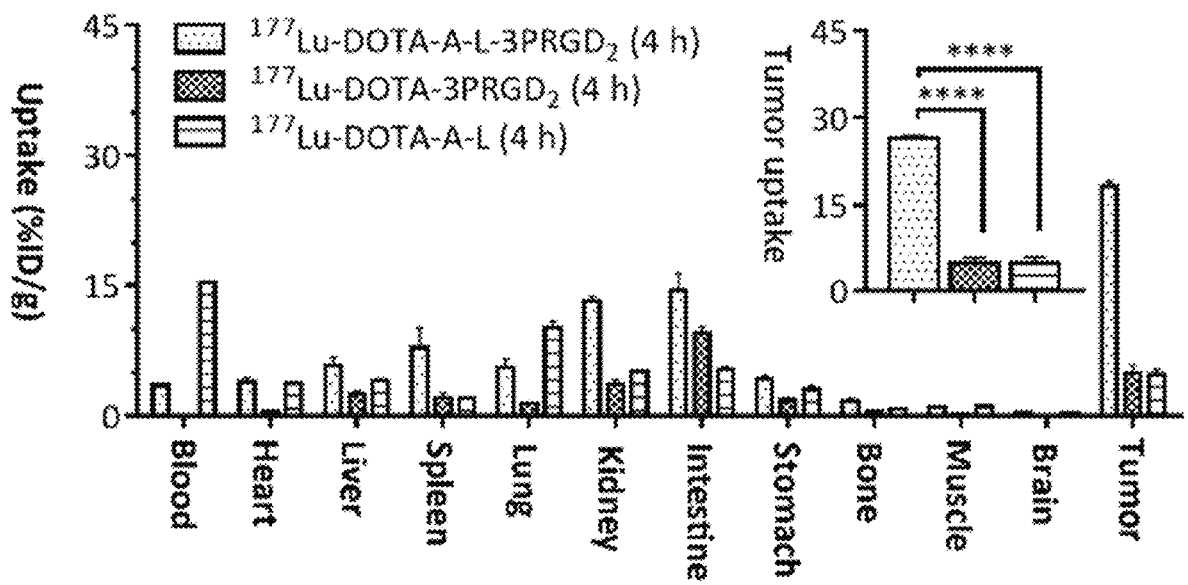
FIGS. 11A-11C: The biodistribution of the molecular probe of Example 7 in the body of the U87-bearing mice.

As shown in FIG. 11A, the tumor uptake values for $^{177}$Lu-DOTA-A-L-3PRGD$_2$, $^{177}$Lu-3PRGD$_2$, and $^{177}$Lu-DOTA-A-L 4 hours after injection are 26.52±0.58, 4.91±0.92%, and 4.80±1.19% ID/g, respectively. The uptake of $^{177}$Lu-DOTA-A-L-3PRGD$_2$ in the tumor is significant higher than these of $^{177}$Lu-3PRGD$_2$ (P<0.0001) and $^{177}$Lu-DOTA-A-L (P<0.0001).

Figure 11B:
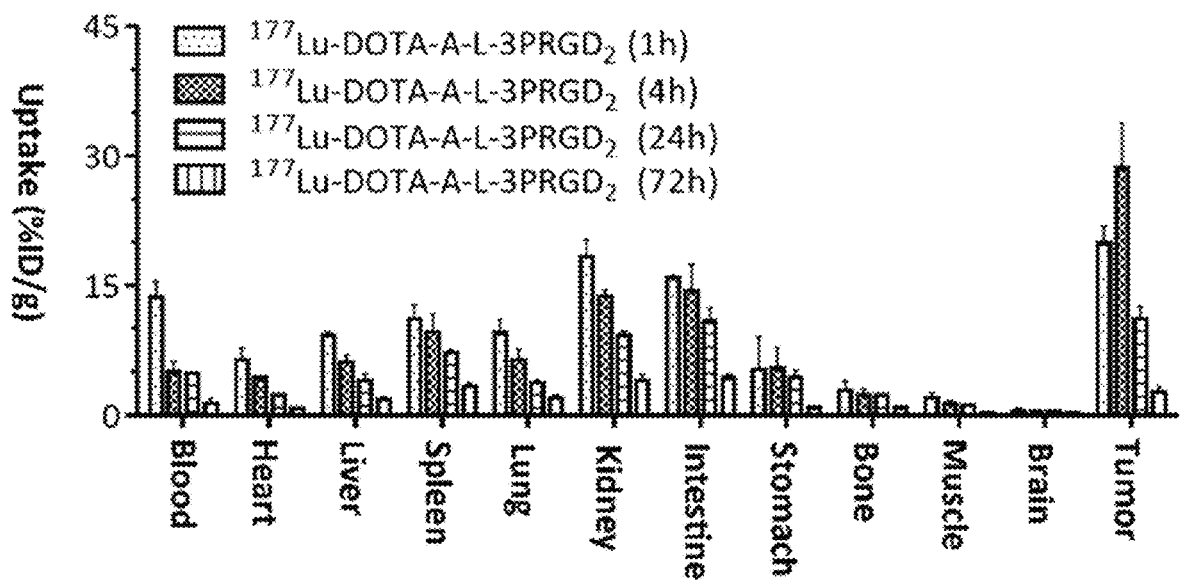

As shown in FIG. 11B, the tumor uptake values for the tumor-bearing mice 1, 4, 24 and 72 hours after injection 19.93±1.99, 28.57±5.27, 11.67±2.80, and 2.66±1.14% ID/g. In addition to the tumor, the uptake of the probe is highest in the kidney and the radioactive probe should have been metabolized through the kidney, which is consistent with the SPECT/CT imaging result. At 4 hr, the ratio of tumor/kidney is over 2-folds (28.57 vs 13.70% ID/g).

Figure 11C:
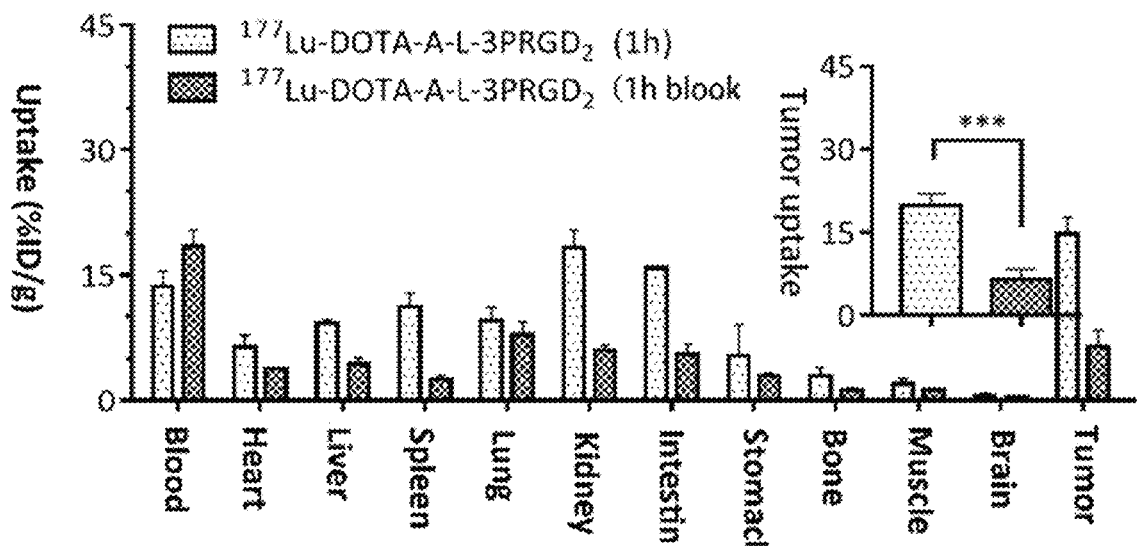

As shown in FIG. 11C, the tumor uptake values in the blockade group and in the normal group 1 hour after administration were 6.41±1.52 and 19.93±1.98% ID/g, respectively. The experimental result demonstrates that the tumor uptake in the blockade group is lower significantly than then non-blockade group (P<0.005) and the uptake of $^{177}$Lu-DOTA-A-L-3PRGD$_2$ in the U87-MG tumor is specific.

EXAMPLE 11

The Targeted Radiotherapy with the Molecular Probe of Example 7

35 of the U87-MG tumor-bearing mice were obtained and randomized into 5 groups (n=7): The mice in Group 1 were injected via tail vain with 100 μL (18 MBq) of $^{177}$Lu-DOTA-A-L-3PRGD$_2$. The mice in Group 2 were injected via tail vain with 100 μL, (18 MBq) of $^{177}$Lu-3PRGD$_2$. The mice in Group 3 were injected via tail vain with 100 μL (18 MBq) of $^{177}$Lu-DOTA-A-L. The mice in Group 4 were injected via tail vain with 100 μL (9 MBq) of $^{177}$Lu-DOTA-A-L-3PRGD$_2$. The tumor-bearing mice in Group 5 were injected with 100 μL of PBS as a control. Changes in the body weight and the tumor volume were monitored every 2 days after injection. The tumor volume reaching to 1000 mm$^3$ was set as the humane endpoint.

Figure 12A:
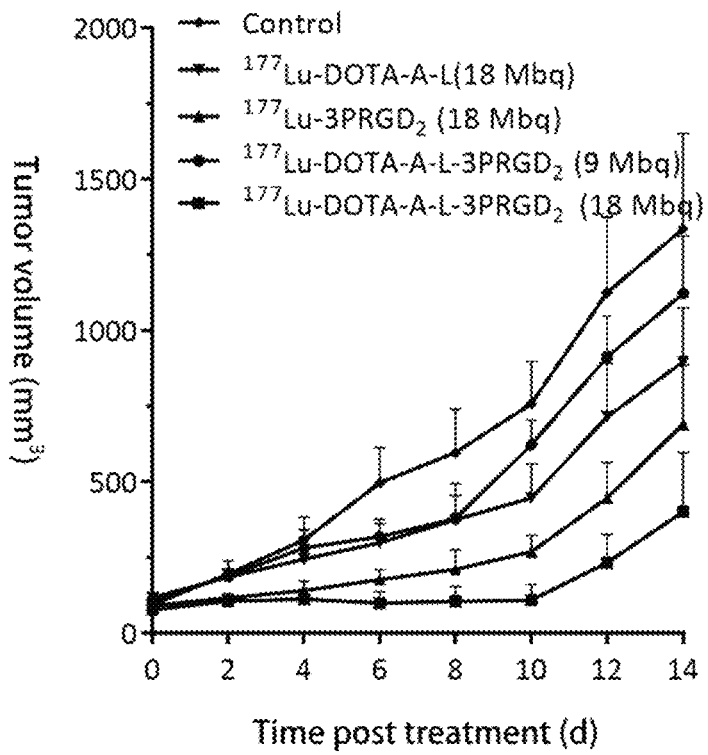
FIGS. 12A-12B: The trending graph for the volume of the tumor radioactively treated with the molecular probe of Example 7 as a function of time.
Figure 12B:
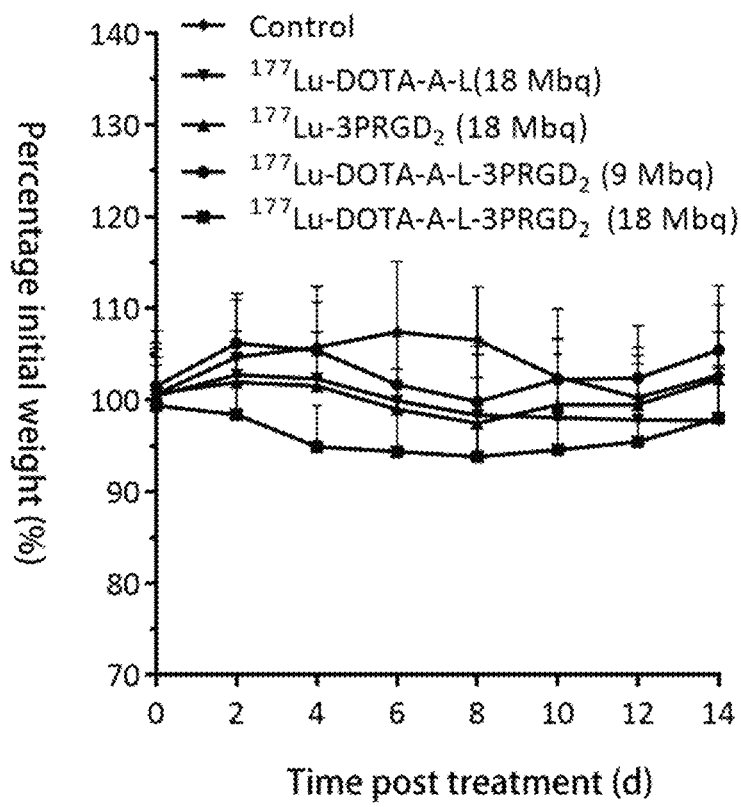

The results are shown in FIGS. 12A-12B. FIGS. 12A and 12B are the trend graphs for the tumor volume as a function of time with the molecular probe of the invention $^{177}$Lu-DOTA-A-L-3PRGD$_2$ at the same doses (18 Mbq) as $^{177}$Lu-3PRGD$_2$ and $^{177}$Lu-DOTA-A-L in the control groups, as well as at a half dose (9 Mbq).

The tumor volume 14 days after administration was: 401.3±195.5 mm$^3$ in the treatment group with 18 MBq of $^{177}$Lu-DOTA-A-L-3PRGD$_2$, 691.3±195.9 mm$^3$ in the treatment group with 9 MBq of $^{177}$Lu-DOTA-A-L-3PRGD$_2$, 1122.4±189.6 mm$^3$ in the treatment group with 18 MBq of $^{177}$Lu-3PRGD$_2$, 897.4±178.0 mm$^3$ in the treatment group with 18 MBq of $^{177}$Lu-DOTA-A-L, and 1336.3±315.4 mm$^3$ in the control group with PBS. The results of the therapy experiment demonstrates that at the injection dose of 18 MBq, the therapeutic effect in $^{177}$Lu-DOTA-A-L-3PRGD$_2$ treatment group is significantly superior to that in the $^{177}$Lu-3PRGD$_2$ treatment groups (p<0.0001) and in the $^{177}$Lu-DOTA-A-L treatment groups (p<0.05). During the treatment, both the changes in body weight of the mice in the three treatment groups mentioned above and the survival metrics were within the normal range. In the same while, the proportions for the changes in the body weights of the mice injected with three probes were all within the normal range, with no apparent acute toxicity. More importantly, the therapeutic effect resulting from reduction of the administered dose of $^{177}$Lu-DOTA-A-L-3PRGD$_2$ to 9 MBq remains significantly higher than that from the doubled dose of $^{177}$Lu-3PRGD$_2$ (p<0.01). The results of the experiment demonstrates that $^{177}$Lu-DOTA-A-L-3PRGD$_2$ has the better therapeutic effect in comparison with the conventional $^{177}$Lu-3PRGD$_2$. It has been shown experimentally that $^{177}$Lu-DOTA-A-L-3PRGD$_2$ can inhibit significantly the tumor growth in the U87-MG bearing mice within 10 days after the targeted treatment with the nuclide. The ratios of the tumor volume on Day 10 against the original volume (V/VO) in the treatment groups and in the control group was 1.4 and 8.0, respectively.

FIG. 12B is the trend graphs for the mouse weight as a function of time with the molecular probe of the invention $^{177}$Lu-DOTA-A-L-3PRGD$_2$ at the same doses (18 Mbq) as $^{177}$Lu-3PRGD$_2$ and $^{177}$Lu-DOTA-A-L in the control groups, as well as at a half dose (9 Mbq). The results of the experiment demonstrates that the BALB/c nude mice are tolerant to $^{177}$Lu-DOTA-A-L-3PRGD$_2$ at the dose of 18 MBq administered. The mouse weight and the routine blood indices in the dosing groups were decreased and then returned to normal. The proportion for mouse weight loss is greatest on Day 6 after administration at the dose of 18 MB and returned to normal on Day 14 after administration. The initial weight percent in the dosing and control groups on Day 6 are 90.8±3.7% and 98.7±5.0%; and the initial weight percent in the dosing and control groups on Day 14 are 100.5±4.1% and 100.7±3.4%. There is no significant changes in the mouse weight during 14 days of treatment with the probe of the invention, compared to the control group. It can be shown that the molecular probe of the invention has fewer side effects and high safety.

EXAMPLE 12

Figure 13A:
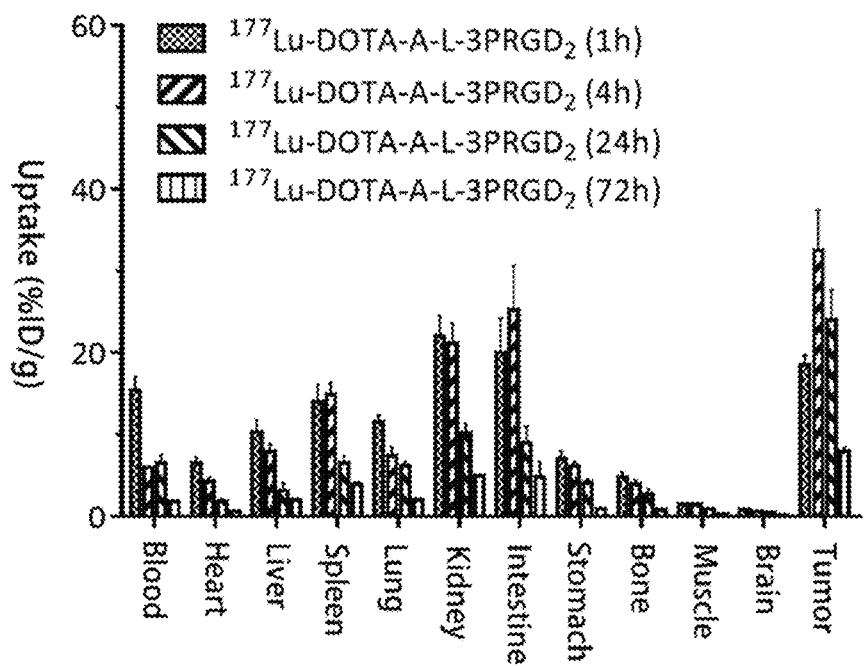
FIGS. 13A-13D: Biodistribution of the molecular probe of Example 7 in the MC-38-bearing mouse model, the graph for SPECT/CT imaging the MC-38-bearing nude mice therewith, and the trending graph for the volume of the tumor radioactively treated therewith as a function of time in the MC-38-bearing mouse model.

Test with the Molecular Probe of Example 7 in MC-38 Mouse Model (1) The Experiment on the Biodistribution of the Molecular Probe of Example 7 In Vivo The results are shown in FIG. 13A. Distribution of the molecular probe of the invention at 1, 4, 24, 72 hrs. It can be known from the result that the uptake of the molecular probe of the invention as a imaging agent is increased first and then decreased in MC-38 tumor over the extended time and reached the highest peak at 4 h, the percent injected doses per gram thereof being 32.51±4.95% ID/g and the highest in all organs. It can be seen that the molecular probe of the invention has very high uptake ratio in the tumor/other organs.

(2) SPECT/CT Imaging of the MC-38-Bearing Nude Mice with the Molecular Probe of Example 7

Figure 13B:
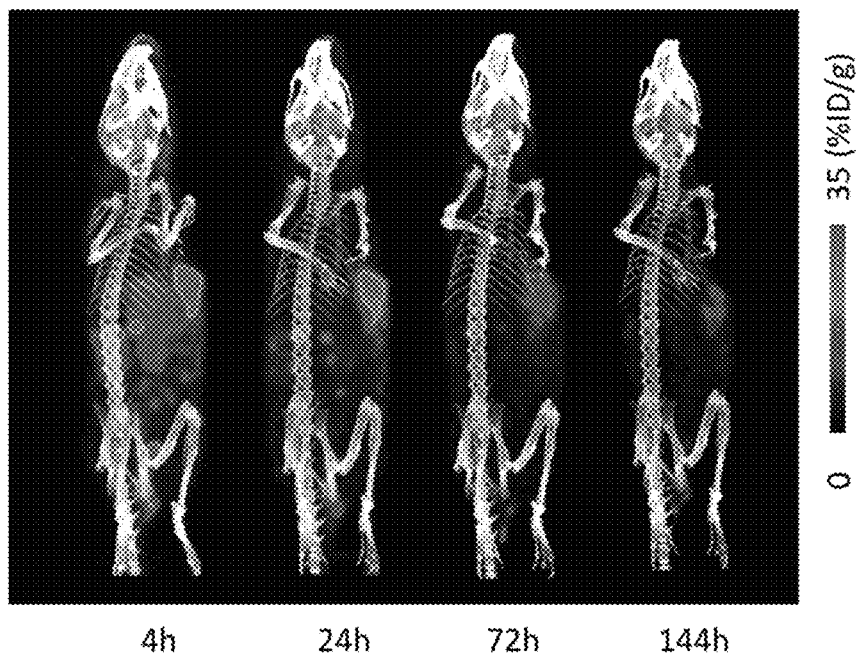

The results are shown in FIG. 13B. The tumor was imaged very well with the probe of the invention at the acquisition time points 1, 4, and 24 hours, and imaged sharply at tumor site with all but almost no background and high contrast ratio. It indicates that the biodistribution property and the pharmacokinetic profile of the molecular probe of the invention is better than those of the original probe.

(3) Changes in Tumor Volume and Mouse Weight after Injection of the Molecular Probe of Example 7

Figure 13C:
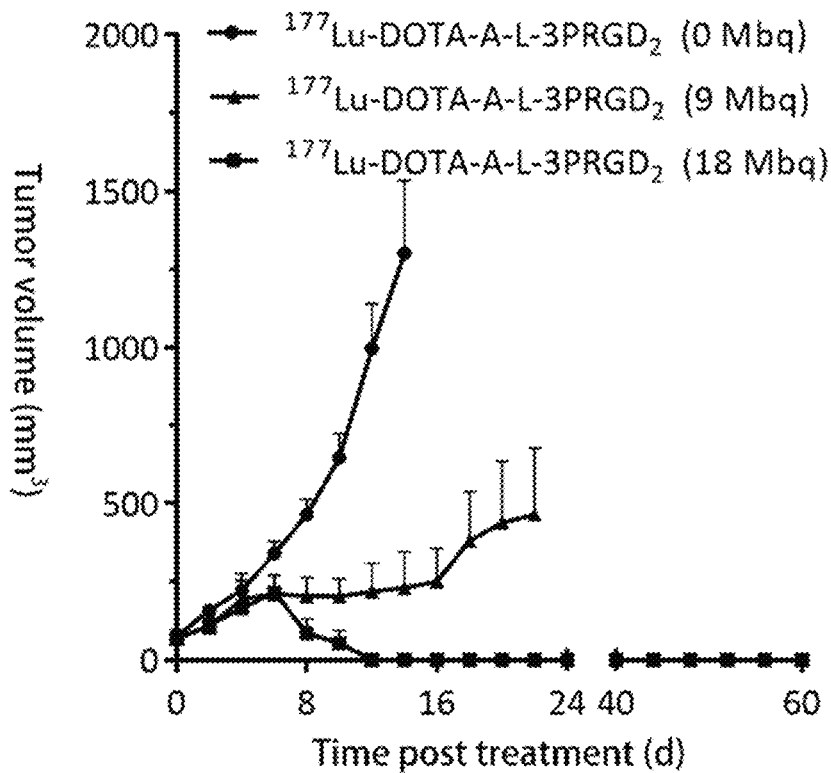
Figure 13D:
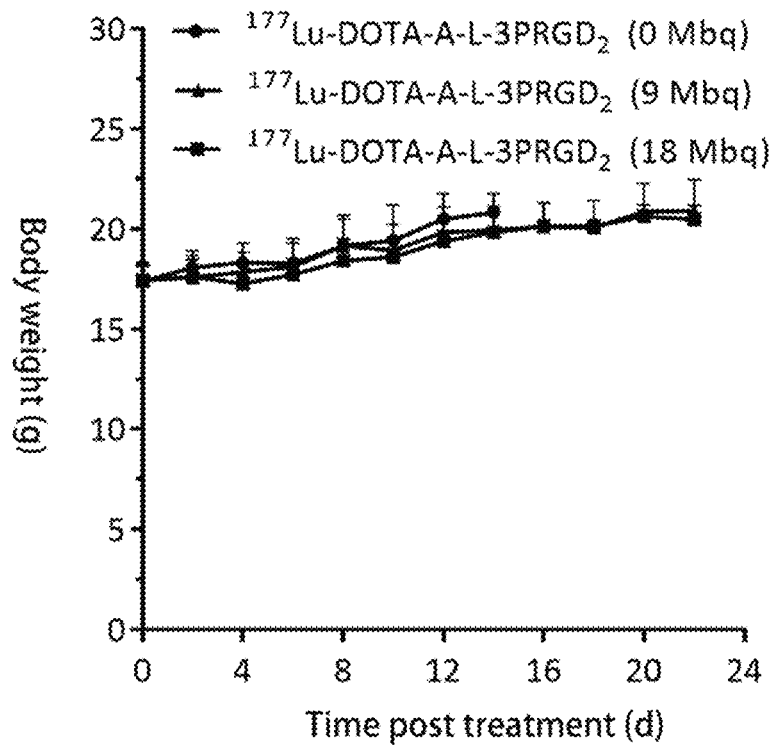

The results are shown in FIGS. 13C and 13D. FIG. 13C is the trend graph for the tumor size as a function of time with the molecular probe of the invention $^{177}$Lu-DOTA-A-L-3PRGD$_2$ at the doses of 18 and 9 Mbq. It can been seen in the FIG. 13C that the tumor was eliminated completely from Day 12 to Day 20 with the molecular probe of the invention at the dose of 18 Mbq, while it was not the case as shown in FIG. 12A Example 11. In comparison with the U87-bearing mice in Example 11, which are immunodeficient, the MC-38-bearing mice in this Example have immune competence themselves and therefore are closer to the functional status in the human patient. This can demonstrate that the molecular probe of the invention can elicit patient's own immunocompetence in treatment of the tumor, enable a better therapeutic effect, and suppress and eliminate the tumor efficiently. FIG. 13D is the trend graph for the mouse weight as a function of time with the molecular probe of the invention at the doses of 18 and 9 Mbq. It can been seen in the FIG. 13D that there is no significant changes in the mouse weight during 20 days of treatment with the probe of the invention. It can be shown that the molecular probe of the invention has fewer side effects and high safety.

EXAMPLE 13

Remodeling of the Tumor Immune Microenvironment with the Targeted Radiotherapy of Example 7

(1) Animal Model

MC-38 (mouse colorectal cancer cell) cells are provided by the Key Research Group, Center for Infection and Immunity, Institute of Biophysics, Chinese Academy of Sciences. The cell was seeded in a DMED high glucose medium containing 10% of thermally inactivated fetal bovine serum and cultured in a humidified incubation chamber at 37° C. with 5% $CO_2$. The C57/BL6 female mice (of 4 to 6 weeks of age) were purchased from Peking University Health Science Department of Laboratory Animal Science and the animal experimentation was in accordance with the stipulations and requirements from the Animal Care and Use Committee, Beijing University. To prepare the tumor-bearing mouse model, 100 μL ($1 \times 10^6$) of MC-38 single cell suspension was injected subcutaneously at the right axillary of the normal mouse and the tumor would be formed in about one week.

(2) Targeted Radiotherapy 21 of the MC-38 tumor-bearing mice were obtained, randomized into 3 groups (n=7), and individually injected intravenously with 100 μL of the different radioactive doses (0, 9 or 18 MBq) of $^{177}$Lu-DOTA-A-L-3PRGD$_2$. Changes in the body weight and the tumor volume were monitored every 2 days after administration. The difference in therapeutic efficacy among the groups was compared. Tumor volume ($mm^3$)=length of the tumor (mm)×width of the tumor (mm)×height of the tumor (mm)×0.5. When the tumor volume is greater than 1200 $mm^3$, the mice was judged to be dead.

Figure 14A:
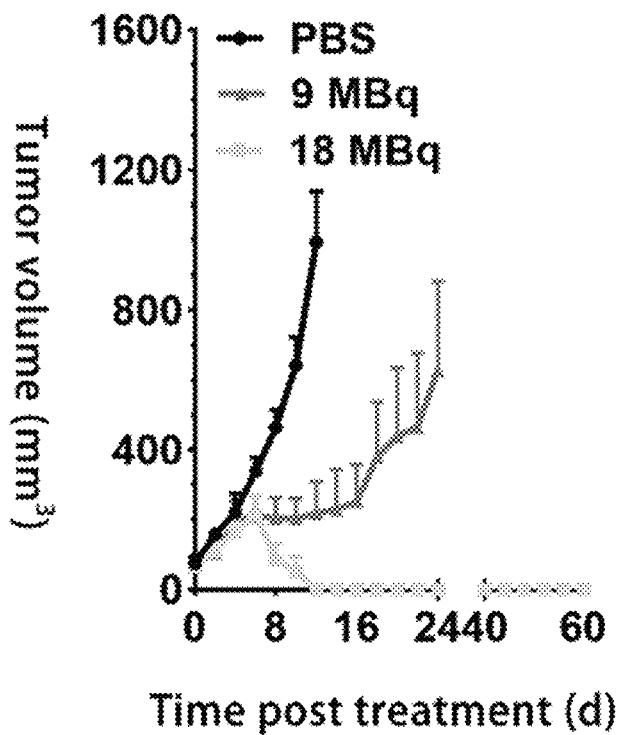
FIGS. 14A-14C: The treatment experiment on $^{177}$Lu-DOTA-A-L-3PRGD$_2$ in the MC-38-bearing mouse model.

The results indicates that: The effect of the targeted radiotherapy with $^{177}$Lu-DOTA-A-L-3PRGD$_2$ is apparent. As shown in FIG. 14A, the tumor was ablated completely 12 days after administration in tumor-bearing mice treated with 18 MBq of $^{177}$Lu-DOTA-A-L-3PRGD$_2$ and did not recur 1 month after cure. Tumor growth was inhibited significantly in the mice treated at the dose of 9 MBq. However, treatment with the low dose of 9 MBq can't inhibit tumor growth for a long term.

Figure 14B:
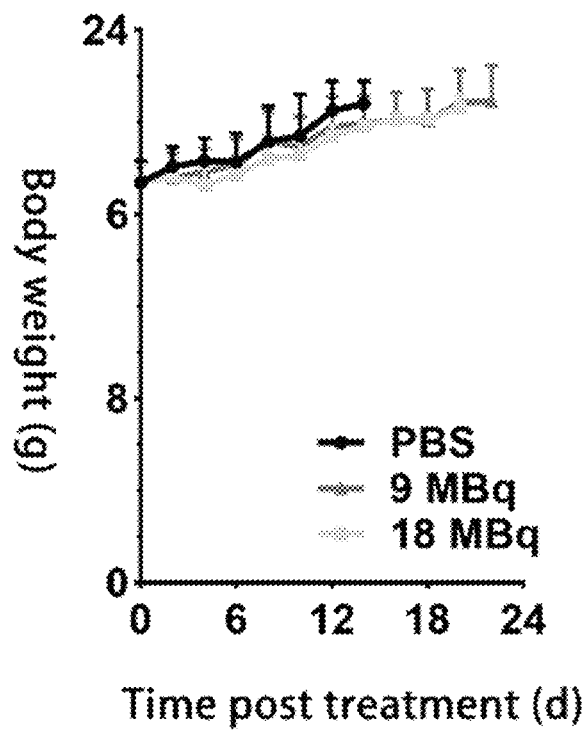

The results indicates that: The targeted radiotherapy with $^{177}$Lu-DOTA-A-L-3PRGD$_2$ has good effectiveness and safety. Although being subject to more apparent loss 2 to 4 days after treatment, the body weights of the mice in the treatment groups (at 9 and 18 MBq) can all returned to the levels equivalent to those in the control group at the end of treatment, as shown in FIG. 14B.

(3) The Anti-Tumor Immune Response Mediated by Effector T Cells

To investigate the anti-tumor effect elicited by the immune system in the targeted radiotherapy with $^{177}$Lu-DOTA-A-L-3PRGD$_2$, the effector T cells in the body of the mouse during the targeted radiotherapy were depleted with an anti-CD 8 antibody, and the difference between the therapeutic effect on the tumor in the depleted mice and the normal mice was compared. 21 of the MC-38-tumor-bearing mice were randomized into 3 groups (n=7): The mice in Group 1 were injected via tail vain with phosphate buffer, serving as an experimental control. The mice in Group 2 were subject to a conventional targeted radiotherapy by injection via tail vain with 18 MBq of $^{177}$Lu-DOTA-A-L-3PRGD$_2$. In addition to receiving 18 MBq of the targeted radiotherapy, the mice in Group 3 were injected via tail vain with 200 μg of the CD8 antibody every 2 days in 0 to 6 days after administration, to deplete effector T cells in the mice. Changes in the tumor volume were monitored every 2 days after administration.

Figure 14C:
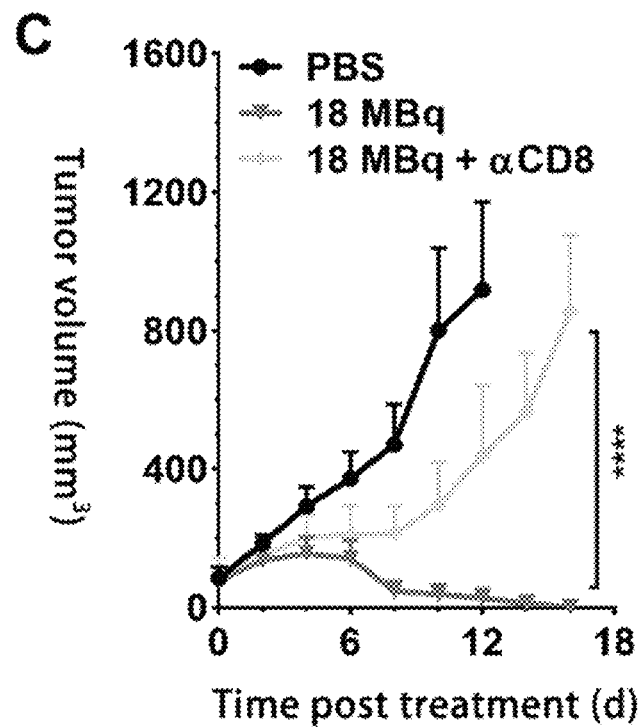

The results indicates that: effector T cells play an important anti-tumor role in the targeted radiotherapy. As shown in FIG. 14C, the therapeutic effect of the targeted radiotherapy at the dose of 18 MBq in the CD8 antibody-depleted mice is substantially impaired in comparison with that in the immune normal mice. Thus, it can be seen that $CD8^+$ T cells playing an important role in the targeted radiotherapy. $^{177}$Lu-DOTA-A-L-3PRGD$_2$ not only kills directly tumor cells, but also can direct the body to generate apparent anti-tumor immunity and play a key role in inhibiting the growth of the tumor.

(4) Changes in Tumor Immune Microenvironment 20 of the MC-38 tumor-bearing mice were randomized into 5 groups (n=4), and individually injected intravenously with 100 μL of the different radioactive doses (0, 6, 9, 12 and 18 MBq) of $^{177}$Lu-DOTA-A-L-3PRGD$_2$, for remodeling the tumor immune microenvironment. On Day 6 after administration, the mice were sacrificed and tumor tissues were removed and prepared into a digested single cell suspension. Infiltration of T lymphocytes within the tumor mass was analyzed by flow cytometry and the change in the expression level of PD-L1 on tumor cells and immune cells was investigated. Tumor tissue was digested with a cell digest solution comprising 1 mg/mL collagenase IV (Worthington) and 0.1 mg/mL DNAase I (Roche). The surface of the T cells was stained at 4° C. for 30 min with the staining antibody used: CD45 (1 μg/mL, Cat. 56-0451-82, eBioscience), CD3e (1 μg/mL, Cat. 25-0031-82, eBioscience), CD8a (2.5 μg/mL, Cat. 11-081-82, eBioscience), CD4 (1 μg/mL, Cat. 45-0042-82, eBioscience). Subsequently, intranuclear staining was performed on T cells using the transcriptional factor staining buffer kit for Foxp3 staining (Cat. 00-523-00, eBioscience) and Foxp3 (1 μg/mL, Cat. 12-4771-82, eBioscience). The tumor cells and the myeloid immune cells were stained on their surface at 4° Cfor 30 min with the antibodies used: CD45 (1 μg/mL, Cat. 56-0451-82, eBioscience), CD11b (1 μg/mL, Cat. 11-0112-82, eBioscience) and CD274 (1 μg/mL, Cat. 12-5982-82, eBioscience). The flow cytometric sample was analyzed with Gallios flow cytometer (Beckman Counter) and the experimental data was processed using the software Flowjo 7.0 (Tree Star).

Figure 15A:
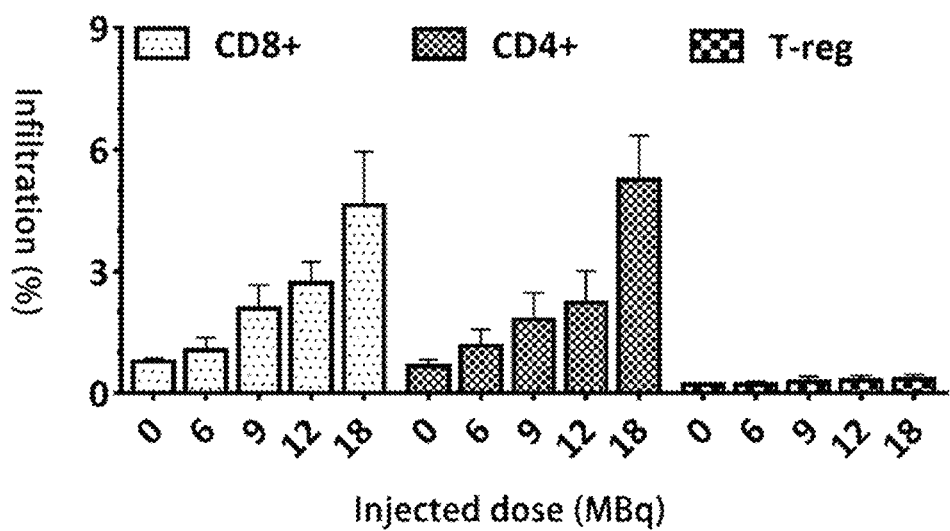
FIGS. 15A-15B: Tumor immune microenvironment at Day 6 after the targeted radiotherapy.

The results indicates that: The targeted radiotherapy can significantly increase infiltration of $CD4^+$ and $CD8^+$ T lymphocytes (rather than T-reg cells) into the tumor tissue. As shown in FIG. 15A, with being stimulated with the different doses (0, 6, 9, 12 and 18 MBq), the proportions of $CD4^+$ T lymphocytes ($CD45^+CD3e^+CD4^+$ cells) infiltrating into the tumor are sequentially 1.04±0.55, 0.76±0.18, 1.17±0.41, 1.82±0.65, 2.24±0.78 and 4.84±0.85%; the proportions of $CD8^+$ T lymphocytes ($CD45^+CD3e^+CD8^+$ cells) infiltrating are sequentially 1.12±0.51, 1.12±0.48, 1.06±0.31, 2.09±0.58, 2.71±0.53 and 4.09±0.93%; and the proportions of T-reg cells ($CD45^+CD3e^+CD4^+$ Foxp-$3^+$ cells) infiltrating are sequentially 0.37±0.27, 0.22±0.08, 0.21±0.07, 0.28±0.13, 0.31±0.13 and 0.34±0.12%.

Figure 15B:
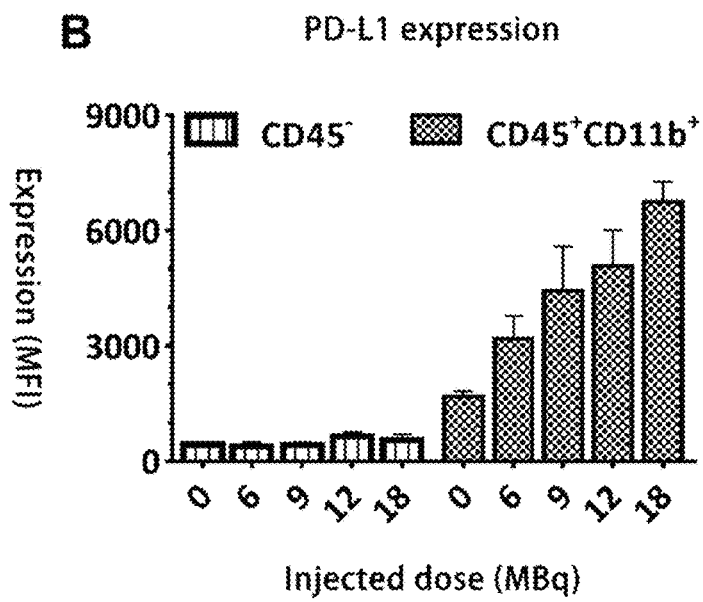

The results indicates that: The targeted radiotherapy can significantly up-regulate the expression level of PD-L1 on the surface of myeloid immune cells (rather than tumor cells) in the tumor. As shown in FIG. 15B, with being stimulated with the different doses (0, 3, 6, 9, 12 and 18 MBq), the amounts of PD-L1 expression (Mean Fluorescence Intensity, MFI) on the tumor cell (CD45-cell) are sequentially 441±68, 511±168, 400±107, 436±64, 659±108 and 556±152; on myeloid immune cells(CD45$^+$CD11b$^+$) sequentially 1681±144, 2938±588, 3187±586, 4444±1140, 5085±926 and 6749±533.

To sum up, the targeted radiotherapy can significantly increase infiltration of the effector T cell in the tumor, and up regulate PD-L1 in the tumor, having an active effect on anti-PD-1/PD-L1 blockade therapy.

EXAMPLE 14

The Imaging-Guided Targeted Radiation in Combination with PD-L1 Blockade (1) Preparation of $^{99m}$Tc-nanoantibody, a PD-L1 Nanoantibody Probe:

$^{99m}$Tc-nanoantibody is prepared with PD-L1 as the biomarker. The selected anti-mouse PD-L1 nanoantibody (MY1523) is labeled with LPTEG-His6 tag at its C-terminus, subject to affinity purification with Ni-agarose gel and to site-specific linkage with transpeptidase Sortase-A. The KD value of the nanoantibody for the murine PD-L1 is 49.70±7.90 nM, with an IC$_{50}$ value of 59.23±0.04 nM and high affinity and specificity.

$^{99m}$Tc-nanoantibody is labeled in a two-step process. First, $^{99m}$Tc-HYNIC-G$_4$K (HYNIC=6-hydrazinonicotinyl, G4K=Gly-Gly-Gly-Gly-Lys) is prepared. 3 μg of HYNIC-G$_4$K (NH$_2$-G$_4$K(HYNIC)-OH), 5 mg of TPPTS (3,3',3"-phosphinidynetris(benzenesulfonic acid) trisodium salt), 6.5 mg tricine (N-[Tris(hydroxymethyl)methyl]glycine) and 74 to 96 MBq of Na$^{99m}$TcO$_4$ rinse fluid are added into 200 μL of succinic acid buffer (250 m M, pH=4.8) and mixed to react at 99° C. for 15 min. The reaction is subject to free cooling, and pH of the mixture is adjusted with 2 M NaOH to reach 7 to 8. Next, MY1523 is labelled with $^{99m}$Tc-HYNIC-G$_4$K to preparation $^{99m}$Tc-MY1523. The mixture solution of 74 MBq of $^{99m}$Tc-HYNIC-G$_4$K, 100 μg of MY1523, and 50 μg of Sortase-A is added into 10 μL (1 M) of CaCl$_2$ and mixed homogenously. Then, the reaction solution reacts at room temperature for 20 min. The product is purified on a high performance exclusion chromatographic column (Superose™ 12, GE healthcare) using a phosphate buffer comprising 0.1% Tween-20 (pH=7.4) as the eluent. Radiochemical purity of the product is determined by thin-layer chromatography using a silica gel-impregnated glass microfiber chromatography paper (ITLC-SG) and normal saline as the developer (Rf values for Na$^{99m}$TcO$_4$ and $^{99m}$Tc-HYNIC-G$_4$K range from 0.7 to 1, and Rf value for $^{99m}$Tc-MY1523 from 0 to 0.3). The prepared $^{99m}$Tc-nanoantibody has the radiochemical purity of >95% and the specific activity of 18.5 to 37 MBq/nmol.

(2) SPECT/CT Imaging

PD-L1 in the tumor is analyzed in a real-time, non-traumatic and dynamic manner by SPECT/CT imaging with $^{99m}$Tc-nanoantibody. SPECT/CT imaging is performed with NanoScan SPECT/CT Small Animal Nuclear Medicine Imaging System, and the energy peak selected for acquisition is of 140 keV, the width of the selected energy peak is 20%, and the acquisition time for a single image is 30 s. When being imaged, the mice are injected via tail vain with 18 MBq of $^{99m}$Tc-nanoantibody and nuclear medicine imaging is conducted 2 hrs. after injection. The mice are anesthetized with isoflurane gas during the imaging. 9 of MC-38-tumor-bearing mice are obtained, divided into 3 groups (n=3), and individually injected intravenously with 100 μL of phosphate buffer and 9 or 18 MBq of $^{177}$Lu-DOTA-A-L-3PRGD$_2$. SPECT/CT imaging with $^{99m}$Tc-nanoantibody is performed at Day 0, 3 and 6 after the targeted radiotherapy and the tumor uptake is quantified as the percent injected doses per gram (% ID/g).

Figure 16A:
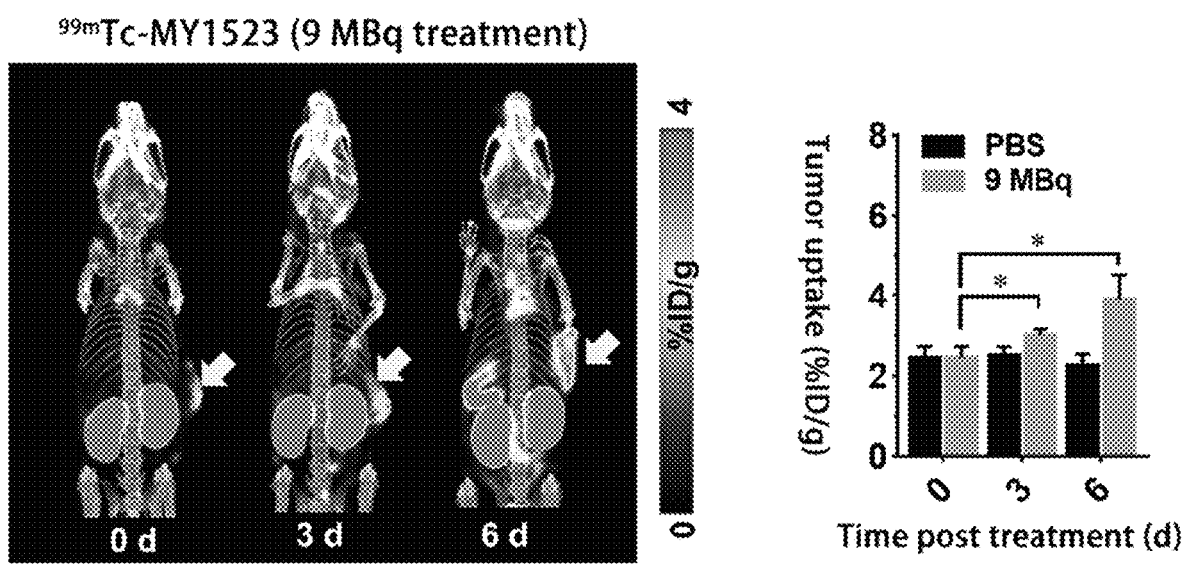
FIGS. 16A-16B: SPECT/CT imaging with $^{99m}$Tc-nanoantibody.
Figure 16B:
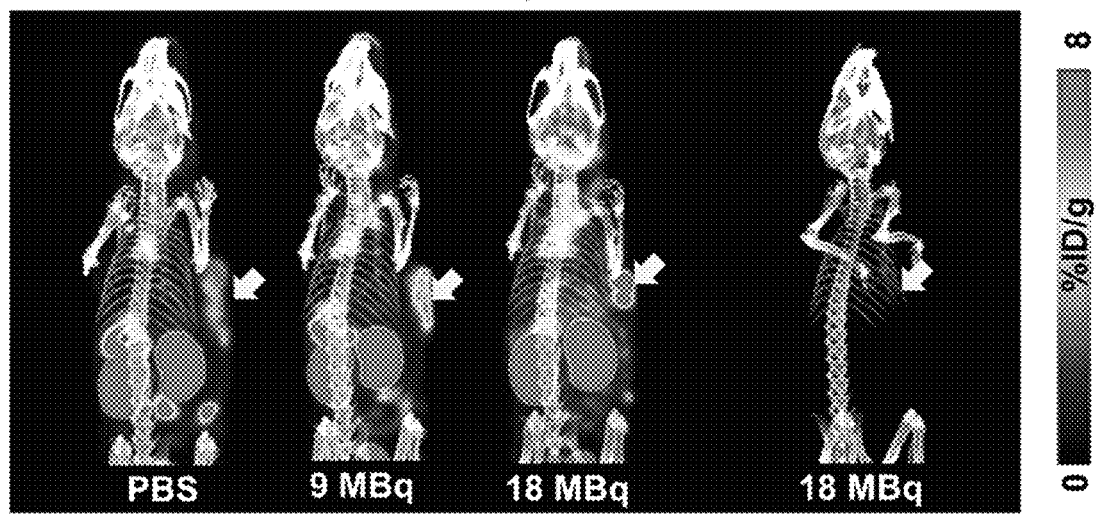

The results indicates that: The uptake of the anti-PD-L1 nanoantibody probe by the tumor is increased significantly after the targeted radiotherapy. As shown in FIG. 16A, the tumor uptake of $^{99m}$Tc-nanoantibody in the low-dose treatment group (9 MBq) is continuously increasing in Days 0 to 6 after administration and highest at Day 6 after treatment, in comparison with that in the control group (PBS). Then, differences in the tumor uptake among the groups at the different doses (0, 9 and 18 MBq) are compared at Day 6 after the targeted radiotherapy. As shown in FIG. 16B, the tumor uptake of $^{99m}$Tc-nanoantibody after treatment with 9 or 18 MBq of the targeted radiotherapy is significantly higher than that in the control group. It has been tested that the acquired $^{99m}$Tc signal is not affected by $^{177}$Lu signal.

(3) Biodistribution

To verify the accuracy of in vivo monitoring the tumor's PD-L1 expression with $^{99m}$Tc-nanoantibody, the linear relationship between the tumor uptake of $^{99m}$Tc-nanoantibody and the tumor's PD-L1 expression is determined. The tumor uptake of the nanoantibody probe is assayed at the tissue level by a biodistribution experiment and PD-L1 expression in the tumor is assayed at the cellular level by flow cytometery after the biodistribution experiment. 20 of the MC-38 tumor-bearing mice are obtained and randomized into 5 groups (n=4). The mice in each group are injected intravenously with 100 μL of the different dose (0, 6, 9, 12 and 18 MBq) of $^{177}$Lu-DOTA-A-L-3PRGD$_2$, for remodeling the tumor immune microenvironment. Biodistribution experiment on $^{99m}$Tc-nanoantibody was conducted after Day 6 of the targeted radiotherapy. The mice were injected via tail vain with 720 kBq of $^{99m}$Tc-nanoantibody and sacrificed 2 h after administration. Blood, tumor tissue and other main tissues or organs were removed, weighed and measured for the radiation counting (cpm). The percent injected dose per gram (% ID/g) of the individual tissues and organs were calculated. The energy peak selected for gamma-counting was from 135 to 155 keV. It was tested that the acquired $^{99m}$Tc signal is not affected by $^{177}$Lu signal. After being measured for radiation counting of the tumor, the tumor tissue was digested immediately to prepare a single cell suspension. PD-L1 expression in the tumor cell (CD 45$^-$) and in the myeloid immune cell (CD45$^+$CD11b$^+$) were separately analyzed by flow analysis.

Figure 17A:
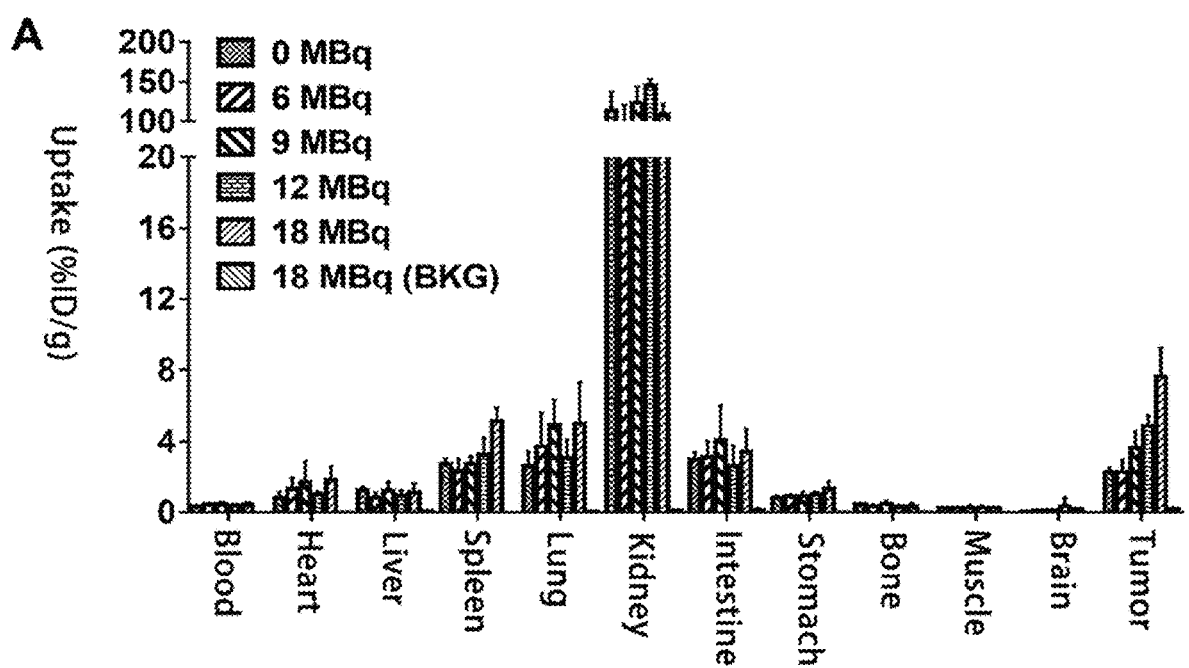
FIGS. 17A and 17B: Biodistribution of $^{99m}$Tc-nanoantibody.
Figure 17B:
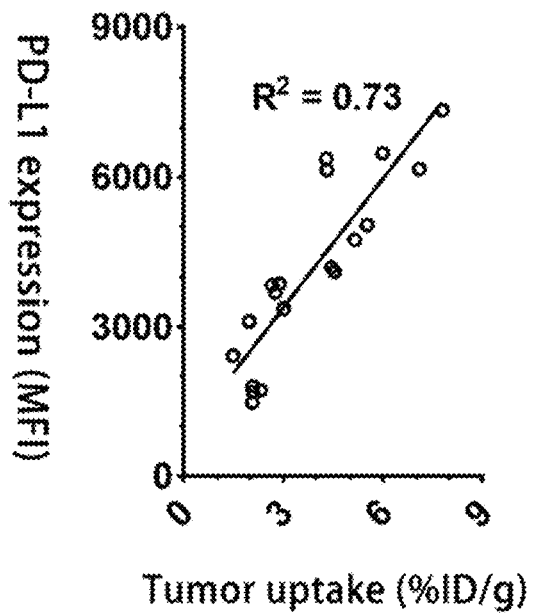

The results indicated that: The expression level of PD-L1 in the tumor can be reflected accurately by determining the tumor uptake of $^{99m}$Tc-nanoantibody. As shown in FIG. 17A, the tumor uptake values of the probe $^{99m}$Tc-MY1523 after treatment with the different therapeutic doses (0, 6, 9, 12 and 18 MBq) were sequentially 2.27±0.26, 2.28±0.69, 3.63±0.94, 4.86±0.58, and 7.66±1.59% ID/g. As shown in FIG. 17B, there is a good linear relationship between the uptake of $^{99m}$Tc-nanoantibody in the tumor tissue and the PD-L1 expression in the tumor ($R^2$=0.80). The result for biodistribution is consistent with the result for imaging. At the same time, the uptake of $^{99m}$Tc-MY1523 probe in the tumor is positively correlated with the expressing of PD-L1 on the infiltrating myeloid immune cells. It has been tested that the acquired $^{99m}$Tc signal is not affected by $^{177}$Lu signal.

(4) The Window for the Dynamic Changes in PD-L1

Change in the expression level of PD-L1 in the tumor over the period of 0 to 6 days after targeted radiotherapy, namely the window for PD-L1 expression, is determined by SPECT/CT imaging with $^{99m}$Tc-nanoantibody. To investigate further the complete expression window for PD-L1, the dynamic changes of PD-L1 in the tumor in 0 to 12 days after targeted radiotherapy were investigated by flow cytometery. 32 of the MC-38 tumor-bearing mice were obtained, randomized into 2 groups (n=16) and injected individually with 100 μL of phosphate buffer or 9 MBq of $^{177}$Lu-DOTA-A-L-3PRGD$_2$. The mice were sacrificed on Days 3, 6, 9 and 12 after administration. Tumor tissues were removed and digested to prepare a single cell suspension. The dynamic changes in the expression level of PD-L1 on tumor cells and myeloid cells were analyzed by flow cytometry.

Figure 18A:
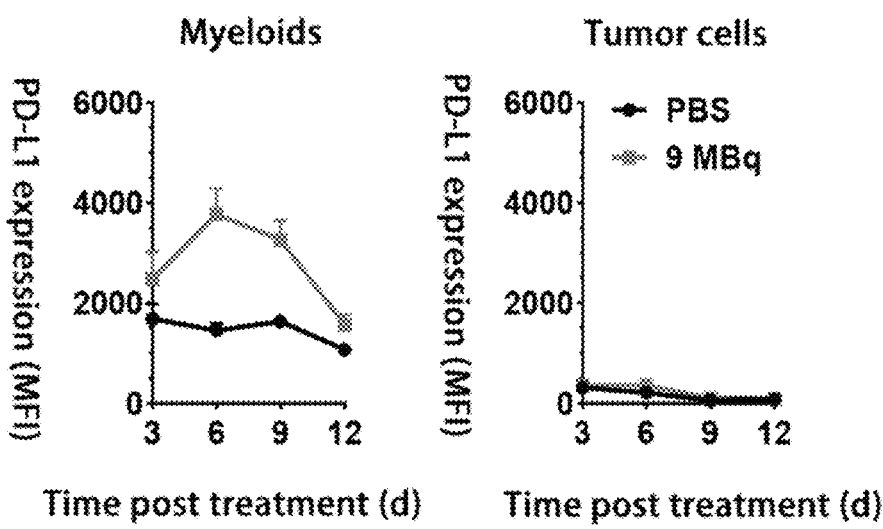
FIGS. 18A and 18B: the therapeutic window of the targeted radiation in combination with PD-L1 blockade.

The results indicates that: PD-L1 expression in the tumor microenvironment after the targeted radiotherapy exhibits a dynamic trend of being high first and then low, and reaches the peak on Day 6 after administration. As shown in FIG. 18A, PD-L1 expression in the tumor microenvironment is continuously up-regulated on Days 3 to 6 after administration and highest on Day 6 after administration. Then, it is continuously decreased on Days 9 to 12 after administration.

(5) Therapeutic Window of PD-L1 Blockade

The single immunotherapy with PD-L1 monoclonal antibody is administered on Days 0 to 12 days after the targeted radiotherapy and the correlation between the therapeutic window for PD-L1 blockade and the window period for the dynamic changes in PD-L1 is investigated on the basis of the dynamic changes in PD-L1, which provides a rationale for the imaging-guided combination treatment of the targeted radiation and PD-L1 blockade. 49 of the MC-38 tumor-bearing mice (60~80 mm$^3$) are obtained and randomized into 7 groups (n=7). The day for administration of the targeted radiotherapy is defined as Day 0. The mice in Group 1 are injected via tail vain with 100 μL of phosphate buffer, serving as an experimental control. The mice in Group 2 are subject to the single targeted radiotherapy by injection via tail vain with 9 MBq of $^{177}$Lu-DOTA-A-L-3PRGD$_2$. In addition to receiving 9 MBq of the targeted radiotherapy, the mice in Groups 3-6 are subject to the combination therapy with 100 μg of the PD-L1 antibody at the different time-points on Days 3, 6, 9, 12, respectively. Changes in the body weight and the tumor volume of the mice were monitored every 2 days. The monitoring ends upon the tumor volume being larger than 1200 mm$^3$ and the mice are sacrificed.

Figure 18B:
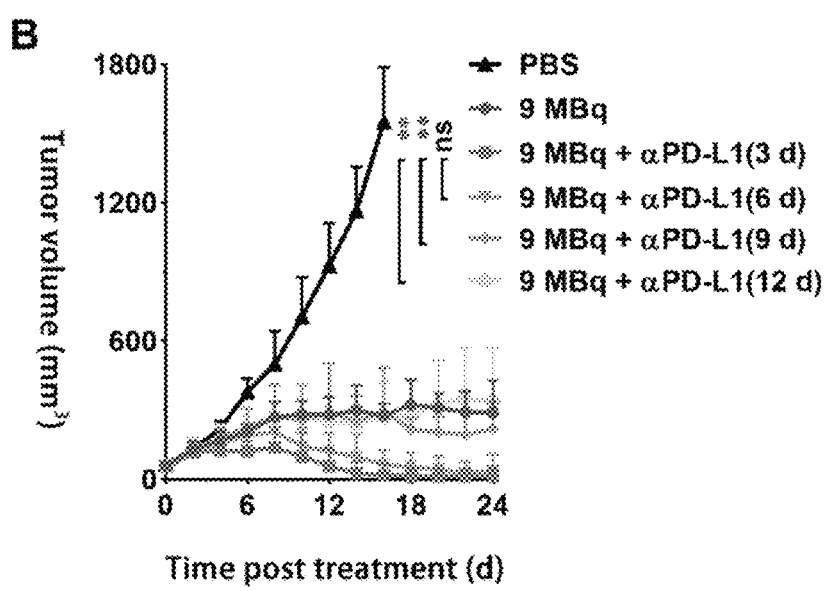

The results indicates that: The effective therapeutic window of the PD-L1 monoclonal antibody is 3 to 6 days after administration and the combined dosing of PD-1/PD-L1 inhibitors was used in the window period of PD-L1 overexpression is favorable for the enhanced efficacy of immunotherapy. As shown in FIG. 18B, the efficacy of the combination treatment with PD-L1 antibody blockade administered on Days 3 to 6 after the targeted radiotherapy significantly outperforms that in the pure targeted radiotherapy groups. However, the efficacy of the combination treatment in which PD-L1 antibody blockade was administered on Days 9 to 12 after the targeted radiotherapy is not apparent.

(6) Synergy of the Combination Therapy

Since the efficacy of PD-L1 blockade therapy is usually superior in the early stage of tumor development over in the advanced tumor, the effect of the immunotherapy in the combination therapy may be affected by tumor size and the synergy of the combination therapy needs to be further confirmed. To verify the synergy of the targeted radiotherapy and PD-L1 immune checkpoint blockade therapy, we compared the combined efficacies of PD-L1 blocking therapy administered before and after the targeted radiotherapy (namely within and out of the window period). 56 of the MC-38 tumor-bearing mice were obtained and randomized into 8 groups (n=7). The day for administration of the targeted radiotherapy is defined as Day 0 and the day for initiation of the experiment as Day −3. The mice in Group 1 were injected via tail vain with 100 μL of phosphate buffer, serving as an experimental control. The mice in Groups 2-4 were subject to the single immunotherapy by injection via tail vain with 100 μg of the PD-L1 antibody at the different time-points on Days −3, 0, and 3, respectively. The mice in Group 5 were subject to the single targeted radiotherapy by injection via tail vain with 9 MBq of $^{177}$Lu-DOTA-A-L-3PRGD$_2$. In addition to receiving 9 MBq of the targeted radiotherapy, the mice in Groups 6-8 were subject to the combination administration of 100 μg of the PD-L1 antibody at the different time-points on Days −3, 0, and 3, respectively. Changes in the body weight and the tumor volume of the mice were monitored every 2 days. Tumor volume of larger than 1200 mm$^3$ was considered fatality.

Figure 19A:
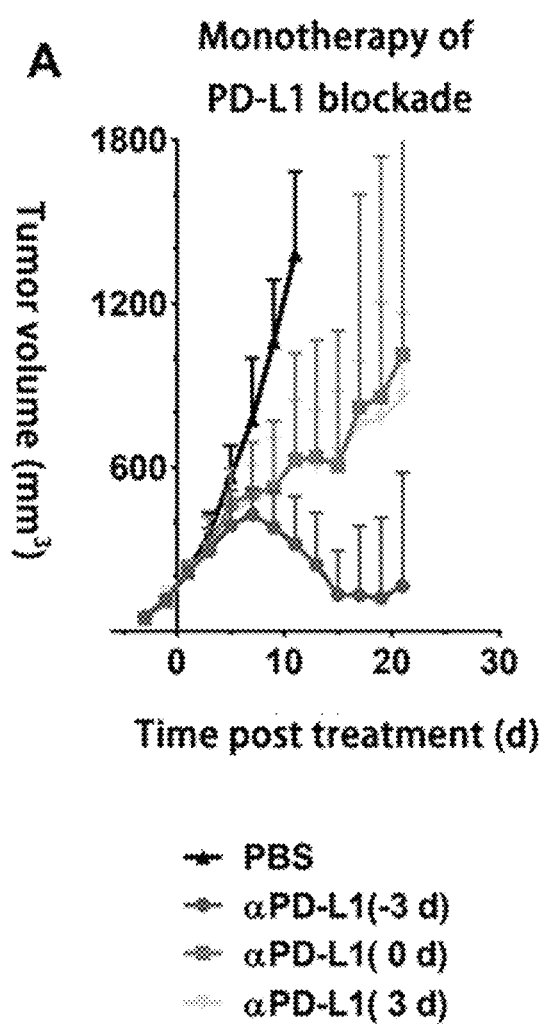
FIGS. 19A-19C: Verification of the synergy for the targeted radiation in combination with PD-L1 blockade.
Figure 19B:
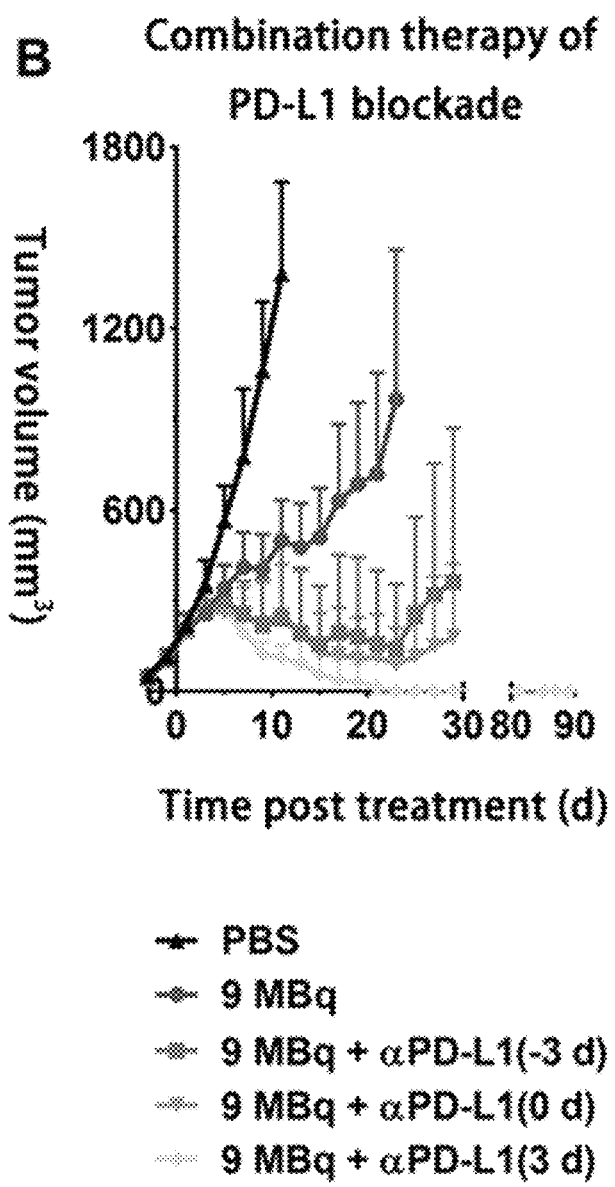
Figure 19C:
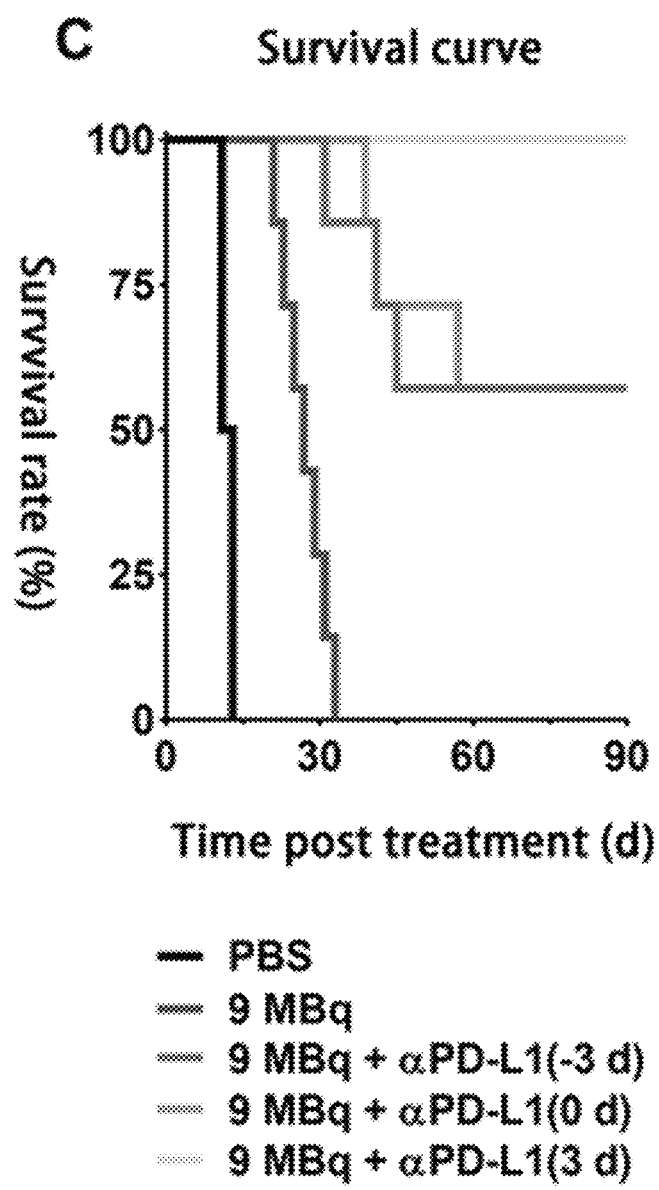

The results indicates that: The effect of the anti-PD-L 1 blockade performed after the targeted radiotherapy is more apparent in comparison with the strategies of early administration and concurrent administration. PD-L1 immune checkpoint blockade therapy administered within the time window during which PD-L1 is increased can significantly inhibit tumor growth, extend survival of the mice, indicating that the combination therapy displays the significant synergy. As shown in FIG. 19A, the therapeutic effect of the single PD-L1 blockade therapy on Day −3 significantly out performs that on Days 0 or 3 and the therapeutic effect of the early PD-L1 blockade treatment significantly out performs the late treatment. As shown in FIG. 19B, the therapeutic efficacy of administering the anti-PD-L1 blockade therapy on Day 3 after the targeted radiotherapy significantly outperforms that of concurrently administering the targeted radiotherapy and the anti-PD-L1 blockade therapy, and significantly outperforms that of administering the anti-PD-L1 blockade therapy on Days 3 before the targeted radiotherapy. As shown in FIG. 19C, in combination treatment with 9 MBq of $^{177}$Lu-DOTA-A-L-3PRGD$_2$, the 90-day survival-ratio of the mice in the groups where the PD-L1 blockade therapy is administered on Days −3, 0 and 3 are sequentially 4/7, 4/7 and 7/7.

The embodiments of the invention have been illustrated as above. However, the present invention is not limited to the above-mentioned embodiments. Any modification and the equivalent replacement thereof, etc. within the spirit and the principles of the invention should be encompassed within the scope of protection of the present invention.

The invention claimed is:

1. A radionuclide-labelled polypeptide complex that is 177Lu-DOTA-A-L-3PRGD$_2$ having a structural formula of

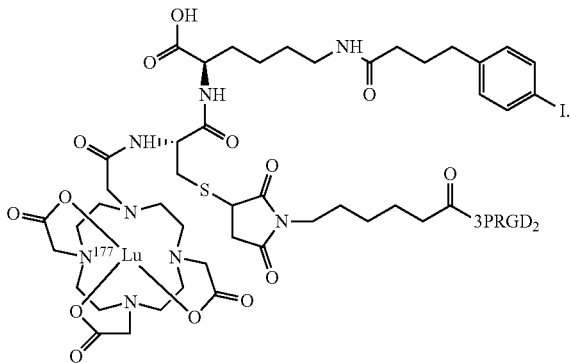

2. A pharmaceutical composition, comprising an effective amount of the radionuclide-labelled polypeptide complex of claim 1.

3. The pharmaceutical composition of claim 2, wherein the radionuclide-labelled polypeptide complex is $^{177}$Lu-DOTA-A-L-3PRGD$_2$, which is a targeted radiation therapy medicament.

4. The pharmaceutical composition of claim 3, further comprising an immunotherapeutic medicament that comprises a PD-1 immune checkpoint inhibitor or a PD-L1 immune checkpoint inhibitor.

5. The pharmaceutical composition of claim 4, wherein the targeted radiation therapy medicament and the immunotherapeutic medicament are separated and adapted to be administered sequentially or in a mixture and adapted to be administered simultaneously.

6. The pharmaceutical composition of claim 4, further comprising a nanoantibody molecular imaging probe.

7. A kit comprising the pharmaceutical composition of claim 6, wherein the targeted radiation therapy medicament, immunotherapeutic medicament, and nanoantibody molecular imaging probe are separately loaded.

8. The pharmaceutical composition of claim 6, wherein the nanoantibody molecular imaging probe is PD-L1 nanoantibody molecular imaging probe.

9. A method for diagnosis or targeted radioactive treatment of an integrin αvβ3-positive tumor, comprising administering to a subject in need thereof an effective amount of a composition, wherein the composition is the pharmaceutical composition of claim 2.

10. The method of claim 9, comprising administering to a subject in need thereof an effective amount of the pharmaceutical composition comprising the radionuclide-labelled polypeptide complex $^{177}$Lu-DOTA-A-L-3PRGD$_2$, which is a targeted radiation therapy medicament.

11. The method of claim 10, wherein the pharmaceutical composition further comprises an immunotherapeutic medicament that comprises a PD-1 immune checkpoint inhibitor or a PD-L1 immune checkpoint inhibitor.

12. The method of claim 11, wherein the immunotherapeutic medicament is administered 3 to 6 days after administering the targeted radiation therapy medicament.

13. The method of claim 12, further comprising administering a nanoantibody molecular imaging probe after administering the targeted radiation therapy medicament and before administering the immunotherapeutic medicament.

14. The method of claim 13, wherein the nanoantibody molecular imaging probe is PD-L1 nanoantibody molecular imaging probe.

* * * * *

UNITED STATES PATENT AND TRADEMARK OFFICE
CERTIFICATE OF CORRECTION

PATENT NO. : 12,357,712 B2
APPLICATION NO. : 17/310604
DATED : July 15, 2025
INVENTOR(S) : Fan Wang et al.

Page 1 of 1

It is certified that error appears in the above-identified patent and that said Letters Patent is hereby corrected as shown below:

In the Claims

At Column 45, Claim 1, Line 3, please replace:
"177Lu-DOTA-A-L-3PRGD$_2$"
With:
--$^{177}$Lu-DOTA-A-L-3PRGD$_2$--

Signed and Sealed this
Fourteenth Day of October, 2025

John A. Squires
*Director of the United States Patent and Trademark Office*